(12) United States Patent
Lin et al.

(10) Patent No.: US 7,253,167 B2
(45) Date of Patent: Aug. 7, 2007

(54) TRICYCLIC-HETEROARYL COMPOUNDS USEFUL AS KINASE INHIBITORS

(75) Inventors: James Lin, Lawrenceville, NJ (US); Stephen T. Wrobleski, Whitehouse Station, NJ (US); Chunjian Liu, Pennington, NJ (US); Katerina Leftheris, Skillman, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 11/170,571

(22) Filed: Jun. 29, 2005

(65) Prior Publication Data

US 2006/0019928 A1    Jan. 26, 2006

Related U.S. Application Data

(60) Provisional application No. 60/584,289, filed on Jun. 30, 2004.

(51) Int. Cl.
 C07D 487/14   (2006.01)
 A61K 31/53    (2006.01)
 A61P 11/00    (2006.01)
 A61P 19/02    (2006.01)
 A61P 37/06    (2006.01)

(52) U.S. Cl. .................... 514/243; 544/184
(58) Field of Classification Search ................ 544/184; 514/243
 See application file for complete search history.

(56) References Cited

U.S. PATENT DOCUMENTS

| | | | |
|---|---|---|---|
| 4,200,750 A | 4/1980 | Warner, Jr. et al. |
| 5,712,279 A | 1/1998 | Biller et al. |
| 5,739,135 A | 4/1998 | Biller et al. |
| 5,760,246 A | 6/1998 | Biller et al. |
| 6,184,231 B1 | 2/2001 | Hewawasam et al. |
| 6,548,529 B1 | 4/2003 | Robl et al. |
| 6,670,357 B2 | 12/2003 | Leftheris et al. |
| 6,706,720 B2 | 3/2004 | Atwal et al. |
| 6,867,300 B2 | 3/2005 | Godfrey, Jr. et al. |
| 6,869,952 B2 | 3/2005 | Bhide et al. |
| 6,906,067 B2 | 6/2005 | Moriarty et al. |
| 6,908,916 B2 | 6/2005 | Mastalerz et al. |
| 6,916,813 B2 | 7/2005 | Atwal et al. |
| 6,916,815 B2 | 7/2005 | Vite et al. |
| 6,933,386 B2 | 8/2005 | Bhide et al. |
| 6,951,859 B2 | 10/2005 | Bhide et al. |
| 2002/0065270 A1 | 5/2002 | Moriety et al. |
| 2003/0139435 A1 | 7/2003 | Ahmed et al. |
| 2003/0186982 A1 | 10/2003 | Godfrey, Jr. |
| 2003/0232831 A1 | 12/2003 | Dyckman et al. |
| 2004/0023992 A1 | 2/2004 | Das et al. |
| 2004/0063707 A1 | 4/2004 | Bhide et al. |
| 2004/0082582 A1 | 4/2004 | Dyckman et al. |
| 2004/0157846 A1 | 8/2004 | Chen et al. |
| 2004/0229877 A1 | 11/2004 | Leftheris et al. |
| 2005/0043306 A1 | 2/2005 | Leftheris et al. |
| 2005/0143398 A1 | 6/2005 | Das et al. |
| 2005/0182058 A1 | 8/2005 | Fink et al. |
| 2005/0209454 A1 | 9/2005 | Swaminathan et al. |

FOREIGN PATENT DOCUMENTS

| | | |
|---|---|---|
| WO | WO 02/062804 | 8/2002 |
| WO | WO 03/080047 | 10/2003 |
| WO | WO 03/090912 | 11/2003 |

OTHER PUBLICATIONS

Wolft Manfred E. "Burger's Medicinal Chemistry, 5ed, Part 1", John Wiley & Sons, 1995, pp. 975-977.*
Banker, G.S. et al, "Modern Pharmaceutics, 3ed.", Marcel Dekker, New York. 1996, pp. 451 and 596.*
Nagarkatti et al. J. Mol. Cell Cardiol. 30(8): 1651-1664, 1998.*
Brunet et al., Esaays Biochem. 32 : 1-16, 1997.*
Herlaar et al. Mol. Med. Today 5(10) 439-447, 1999.*
Graninger et al. Curr. Opin. Rheumatol. 13(3): 209-213.*
U.S. Appl. No. 09/573,829, filed May 18, 2000.
U.S. Appl. No. 11/019,899, filed Dec. 22, 2004.
U.S. Appl. No. 11/111,144, filed Apr. 21, 2005.
U.S. Appl. No. 11/152,650, filed Jun. 14, 2005.
U.S. Appl. No. 11/157,460, filed Jun. 21, 2005.
U.S. Appl. No. 11/168,682, filed Jun. 28, 2005.
U.S. Appl. No. 11/199,746, filed Aug. 9, 2005.
U.S. Appl. No. 60/620,784, filed Oct. 21, 2004.
Ahn, H.-S. et al., "Potent Tetracyclic Guanine Inhibitors of PDE1 and PDE5 Cyclic Guanosine Monophosphate Phosphodiesterases with Oral Antihypertensive Activity", J. Med. Chem., vol. 40, No. 14, pp. 2196-2210 (1997).
Bundgaard, H., Chapter 5: "Design and Application of Prodrugs", A Textbook of Drug Design and Development, Harwood Academic Publishers, Publ., Krogsgaard-Larsen, P. et al., eds., pp. 113-191 (1991).
Bundgaard, H., ed., Design of Prodrugs, Elsevier Science Publishers B.V., publ. (1985) (table of contents).
Henry, J.R. et al., "p38 mitogen-activated protein kinase as a target for drug discovery", Drugs of the Future, vol. 24, No. 12, pp. 1345-1354 (1999).

(Continued)

Primary Examiner—Venkataraman Balasubramanian
(74) Attorney, Agent, or Firm—Maureen P. O'Brien; Joseph C. Wang

(57) ABSTRACT

The present invention relates to compounds having the formula,

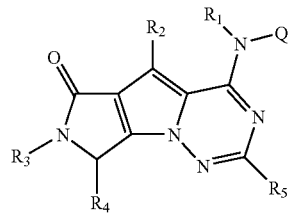

wherein, Q is optionally substituted aryl or heteroaryl, $R_1$ is hydrogen or $C_{1-4}$alkyl, and $R_2$, $R_3$, $R_4$ and $R_5$ are hydrogen or optional substituents as defined in the specification.

17 Claims, No Drawings

OTHER PUBLICATIONS

Jaffari, G.A. et al., "Some Oxidation Reactions of Monochloramine", J. Chem. Soc. (C), pp. 823-826 (1971).

Kakeya, N. et al., "Studies on Prodrugs of Cephalosporins. I. Synthesis and Biological Properties of Glycyloxybenzoyloxmethyl and Glycylaminobenzoyloxymethyl Esters of 7β-[2-(2-Aminothiazol-4-yl)-(Z)-2-methoxyiminoacetamido]-3-methyl-3-cephem-4-carboxylic Acid", Chem. Pharm Bull., vol. 32, No. 2, pp. 692-698 (1984).

Manning, G. et al., "The Protein Kinase Complement of the Human Genome", Science, vol. 298, pp. 1912-1916, 1933-1934 (2002).

Moreland, L.W. et al., "Etanercept Therapy in Rheumatoid Arthritis: A Randomized, Controlled Trial", Ann. Intern. Med., vol. 130, No. 6, pp. 478-486 (1999).

Nielsen, N.M. et al., "Glycolamide Esters as Biolabile Prodrugs of Carboxylic Acid Agents: Synthesis, Stabilty, Bioconversion, and Physicochemical Properties", Journal of Pharmaceutical Sciences, vol. 77, No. 4, pp. 285-298 (1988).

Raingeaud, J. et al., "MKK3- and MKK6-Regulated Gene Expression Is Mediated by the p38 Mitogen-Activated Protein Kinase Signal Transduction Pathway", Molecular and Cellular Biology, vol. 16, No. 3, pp. 1247-1255 (1996).

Rankin, E.C.C. et al., "The Therapeutic Effects of an Engineered Human Anti-Tumour Necrosis Factor Alpha Antibody (CDP571) in Rheumatoid Arthritis", British Journal of Rheumatology, vol. 34, No. 4, pp. 334-342 (1995).

Salituro, F.G. et al., "Inhibitors of p38 MAP Kinase: Therapeutic Intervention in Cytokine-Mediated Diseases", Current Medicinal Chemistry, vol. 6, No. 9, pp. 807-823 (1999).

Selič, L. et al., "Transformations of Alkyl 2-(2,2-Disubstituted-ethenyl)amino-3-dimethylaminoprop-2-enoates: Synthesis of Alkyl 3,4-Disubstituted- and Alkyl 1-Acyl-3,4-disubstituted Pyrrole-2-carboxylates", Synthesis, No. 3, pp. 479-482 (1999).

Svete, J. et al., "2-Benzoyl-2-ethoxycarbonylvinyl-1 and 2-Benzoylamino-2-methoxycarbonylvinyl-1 as N-Protecting Groups in Peptide Synthesis. Their Application in the Synthesis of Dehydropeptide Derivatives Containing N-Terminal 3-Heteroarylamino-2,3-dehydroalanine", J. Heterocyclic Chem., vol. 34, pp. 177-193 (1997).

Toplak, R. et al., "Ethyl 2-(2-acetyl-2-ethoxycarbonyl-1-ethenyl)amino-3-dimethylaminopropenoate in the Synthesis of Heterocyclic Systems. The Synthesis of Substituted 3-Aminoazolo- and -Azinopyrimidinones, Pyridopyridinones and Pyranones", Heterocycles, vol. 50, No. 2, pp. 853-866 (1999).

Widder, K.J. et al., eds., Section III: "Prodrugs", Methods in Enzymology, vol. 112, Academic Press, Inc., publ., pp. 309-396 (1985).

Yet, L., "Peptide Coupling Reagents: Names, Acronyms and References", Technical Reports, Albany Molecular Research, Inc., vol. 4, No. 1, pp. 1-7 (1999).

Branger, J., et al., "Anti-Inflammatory Effects of a p38 Mitogen-Activated Protein Kinase Inhibitor During Human Endotoxemia" The Journal of Immunology, vol. 168, pp. 4070-4077, (2002).

Davis, J. C., Jr., "Understanding the Role of Tumor Necrosis Factor Inhibition in Ankylosing Spondylitis", Seminars in Arthritis and Rheumatism, vol. 34, pp. 668-677, (2004).

Gottlieb, A. B., et al., TNF Inhibition Rapidly Down-Regulates Multiple Proinflammatory Pathways in Psoriasis Plaques[1], The Journal of Immunology, vol. 175, pp. 2721-2729, (2005).

Hideshima, T. et al, "Targeting p38 MAPK inhibits multiple myeloma cell growth in the bone marrow milieu", Blood, vol. 101(2), pp. 703-706, (2003).

Johansen, C., et al., "Protein Expression of TNF-α in Psoriatic Skin Is Regulated at a Posttranscriptional Level by MAPK-Activated Protein Kinase 2[1]", The Journal of Immunology, vol. 176, pp. 1431-1438, (2006).

Johansen, C., et al., "The mitogen-activated protein kinases p38 and KRK1/2 are increased in lesional psoriatic skin", British Journal of Dermatology, vol. 152, pp. 37-42, (2005).

Kumar, S., et al., "P38 MAP Kinases: Key Signalling Molecules as Therapeutic Targets for Inflammatory Diseases", vol. 2, pp. 717-726, (2003).

Mease, P. J., et al., "Psoriatic arthritis treatment: biological response modifiers", Ann. Rheum. Dis., vol. 64 (Suppl. II), pp. ii78-ii82, (2005).

Navas, TA, et al., Inhibition of p38α MAPK enhances proteasome inhibitor-induced apoptosis of myeloma cells by modulating Hsp27, Bcl-$X_L$, MCl-1 and p53 levels in vitro and inhibits tumor growth in vivo, Leukemia, 1-11 (2006).

Papp. K. A., "The long-term efficacy and safety of new biological therapies for psoriasis", Arch. Dermatol. Res. vol. 298, pp. 7-16, (2006).

Saklatvala, J., "The p38 MAP Kinase pathway as a therapeutic target in inflammatory disease", Current Opinion in Pharmacology, vol. 4, pp. 372-377, (2004).

Waetzig G. H., "p38 Mitogen-Activated Protein Kinase Is Activated and Linked to TNF-α Signaling in Inflammatory Bowel Disease[1]", The Journal of Immunology, vol. 168, pp. 5342-5351, (2002).

Bundgaard, H., "Means to Enhance Penetration: Prodrugs as a means to improve the delivery of peptide drugs", Advanced Drug Delivery Reviews, vol. 8, pp. 1-38 (1992).

Ettmayer, P. et al., "Lessons Learned from Marketed and Investigational Prodrugs", Journal of Medicinal Chemistry, vol. 47, No. 10, pp. 2393-2404 (2004).

Greene, T.W. et al., Protective Groups in Organic Synthesis, Third Edition, John Wiley & Sons, Inc., publ., pp. xi-xii (table of contents) (1999).

* cited by examiner

TRICYCLIC-HETEROARYL COMPOUNDS USEFUL AS KINASE INHIBITORS

CROSS-REFERENCE TO RELATED APPLICATION

This application claims priority benefit under Title 35 § 119(e) of U.S. provisional Application No. 60/584,289, filed Jun. 30, 2004, the contents of which are herein incorporated by reference.

FIELD OF THE INVENTION

This invention relates to tricyclic-heteroaryl compounds useful for treating p38 kinase-associated conditions. The invention further pertains to pharmaceutical compositions containing at least one compound according to the invention useful for treating p38 kinase-associated conditions, and methods of inhibiting the activity of p38 kinase in a mammal.

BACKGROUND OF THE INVENTION

A large number of cytokines participate in the inflammatory response, including IL-1, IL-6, IL-8 and TNF-α. Overproduction of cytokines such as IL-1 and TNF-α are implicated in a wide variety of diseases, including inflammatory bowel disease, rheumatoid arthritis, psoriasis, multiple sclerosis, endotoxin shock, osteoporosis, Alzheimer's disease, and congestive heart failure, among others [Henry et al., *Drugs Fut.*, Vol. 24 (1999), at pp. 1345-54; Salituro et al., *Curr. Med. Chem.*, Vol. 6 (1999), at pp. 807-823]. Evidence in human patients indicates that protein antagonists of cytokines are effective in treating chronic inflammatory diseases, such as, for example, monoclonal antibody to TNF-α (Enbrel) [Rankin et al., *Br. J. Rheumatol.*, Vol. 34 (1995), at pp. 334-42], and soluble TNF-α receptor-Fc fusion protein (Etanercept) [Moreland et al., *Ann. Intern. Med.*, Vol. 130 (1999), at pp. 478-86].

The biosynthesis of TNF-α occurs in many cell types in response to an external stimulus, such as, for example, a mitogen, an infectious organism, or trauma. Important mediators of TNF-α production include the mitogen-activated protein (MAP) kinases, a family of Ser/Thr protein kinases that activate their substrates by phosphorylation. The MAP kinases are activated in response to various stress stimuli, including but not limited to proinflammatory cytokines, endotoxin, ultraviolet light, and osmotic shock.

One important MAP kinase is p38 kinase, also known as cytokine suppressive anti-inflammatory drug binding protein (CSBP) or IK. Activation of p38 requires dual phosphorylation by upstream MAP kinase kinases (MKK3 and MKK6) on threonine and tyrosine within a Thr-Gly-Tyr motif characteristic of p38 isozymes. There are four known isoforms of p38, i.e., p38-α, p38β, p38γ, and p38δ. The α and β isoforms are expressed in inflammatory cells and are key mediators of TNF-α production. Inhibiting the p38α and β enzymes in cells results in reduced levels of TNF-α expression. Also, administering p38α and β inhibitors in animal models of inflammatory disease has established the effectiveness of these inhibitors in treating those diseases. The present invention provides tricycle pyrrolotriazine compounds, useful as kinase inhibitors, in particular, as inhibitors of p38α and β kinase.

DESCRIPTION OF THE INVENTION

The present invention pertains to compounds having the formula (I),

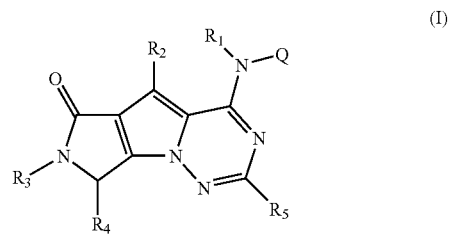

(I)

wherein:
Q is aryl or heteroaryl, wherein said aryl or heteroaryl is optionally substituted with 0 to 2 $R_6$, 0 to 2 $R_7$, and 0 to 1 $R_8$;

$R_1$ is hydrogen or $C_{1-4}$alkyl;

$R_2$ and $R_4$ are independently selected from hydrogen, alkyl, substituted alkyl, alkenyl, substituted alkenyl, halogen, cyano, nitro, amino, alkylamino, hydroxy, alkoxy, substituted alkoxy, alkylthio, substituted alkylthio, cycloalkyl, substituted cycloalkyl, aryl, substituted aryl, heterocyclo, substituted heterocyclo, heteroaryl, and substituted heteroaryl;

$R_3$ and $R_5$ are independently selected from hydrogen, alkyl, substituted alkyl, alkenyl, substituted alkenyl, cycloalkyl, substituted cycloalkyl, aryl, substituted aryl, heterocyclo, substituted heterocyclo, heteroaryl, and substituted heteroaryl;

$R_6$, $R_7$ and $R_8$ are at each occurrence independently selected from hydrogen, alkyl, substituted alkyl, alkenyl, substituted alkenyl, halogen, cyano, nitro, —$OR_9$, —$SR_9$, —S(=O)$R_{11}$, —S(=O)$_2R_{11}$, —P(=O)$_2R_{10}$, —S(=O)$_2$$OR_{11}$, —P(=O)$_2$$OR_{10}$, —$NR_9R_{10}$, —$NR_9$S(=O)$_2R_{11}$, —$NR_9$P(=O)$_2R_{10}$, —S(=O)$_2NR_9R_{10}$, —P(=O)$_2NR_9R_{10}$, —C(=O)$OR_9$, —C(=O)$R_9$, —C(=O)$NR_9R_{10}$, —OC(=O)$R_9$, —OC(=O)$NR_9R_{10}$, —$NR_9$C(=O)$OR_{10}$, —$NR_{12}$C(=O)$NR_9R_{10}$, —$NR_{12}$S(=O)$_2NR_9R_{10}$, —$NR_{12}$P(=O)$_2NR_9R_{10}$, —$NR_9$C(=O)$R_{10}$, —$NR_9$P(=O)$_2R_{10}$, cycloalkyl, substituted cycloalkyl, aryl, substituted aryl, heterocyclo, substituted heterocyclo, heteroaryl, and substituted heteroaryl;

$R_9$, $R_{10}$, and $R_{12}$ are independently at each occurrence selected from hydrogen, alkyl, substituted alkyl, alkenyl, substituted alkenyl, cycloalkyl, substituted cycloalkyl, heterocycle, substituted heterocycle, aryl, substituted aryl, heteroaryl and substituted heteroaryl, or alternatively, $R_9$ and $R_{10}$ when attached to the same nitrogen atom as in —$NR_9R_{10}$ can be taken together to form a heterocyclo, heteroaryl, substituted heterocyclo, or substituted heteroaryl;

$R_{11}$ is selected from alkyl, substituted alkyl, alkenyl, substituted alkenyl, cycloalkyl, substituted cycloalkyl, heterocycle, substituted heterocycle, aryl, substituted aryl, heteroaryl and substituted heteroaryl;

and/or pharmaceutically-acceptable salts, isomers and/or prodrugs thereof.

According to another aspect of the invention, there is provided a method of modulating p38 kinase in a mammal by administering a compound of formula (I) and/or at least one salt, isomer and/or prodrug thereof, to said mammal.

According to another aspect of the invention, there is provided a pharmaceutical composition comprising at least one compound according to formula (I), and/or at least one salt, isomer and/or prodrug thereof, in a pharmaceutically-acceptable carrier or diluent. According to another aspect of the invention, there is provided a method of treating an inflammatory disorder comprising administering to a patient a pharmaceutical composition comprising at least one compound according to formula (I), and/or at least one salt, isomer, and/or prodrug thereof, in a pharmaceutically-acceptable carrier or diluent.

When reference is made hereinafter to a selection of moieties for variables (e.g., $R_1$, $R_2$, $R_3$, $R_4$, $R_5$, $R_6$, $R_7$, etc.) as recited herein for compounds of formula (I) (e.g., in the "alternative embodiments" section below, and in the methods of preparation), this is intended to refer to the selections for the corresponding variables as recited immediately above.

Definitions

The initial definition provided for a group or term herein applies to that group or term throughout the present specification and claims herein individually or as part of another group, unless otherwise indicated.

The terms "alkyl" and "alk" refer to a straight or branched chain alkane (hydrocarbon) radical containing from 1 to 12 carbon atoms, preferably 1 to 6 carbon atoms. Exemplary "alkyl" groups include methyl, ethyl, propyl, isopropyl, 1-methylpropyl, n-butyl, t-butyl, isobutyl, pentyl, hexyl, isohexyl, heptyl, dimethylpentyl, diethylpentyl, octyl, 2,2,4-trimethylpentyl, nonyl, decyl, undecyl, dodecyl, and the like. The term "$C_1$-$C_4$ alkyl" refers to a straight or branched chain alkane (hydrocarbon) radical containing from 1 to 4 carbon atoms, such as methyl, ethyl, propyl, isopropyl, n-butyl, t-butyl, and isobutyl. A lower alkyl is a "$C_1$-$C_4$ alkyl." When alkyl, lower alkyl, or $C_1$-$C_4$alkyl is used as a suffix following another named group, such as hydroxyalkyl, hydroxyl(lower alkyl), or hydroxyl($C_1$-$C_4$alkyl), this is intended to refer to an alkyl, lower alkyl, or $C_1$-$C_4$alkyl having bonded thereto one, two or three of the other, specifically-named group(s) at any point of attachment on either the straight or branched chain of the alkyl. As a further example, arylalkyl includes groups such as benzyl, phenylethyl, or biphenyl. When the term "substituted" is used with such groups, as in "substituted arylalkyl" or "substituted alkoxyalkyl," it should be understood that either the alkyl moiety, the other named moiety, or both, may be substituted with groups selected from those recited herein as appropriate for the named moiety, e.g., for the alkyl moiety, groups may be selected from those recited below for substituted alkyl, and for the other, specifically-named group, groups may be selected from those recited below for that named group.

"Substituted alkyl" refers to an alkyl group as defined above substituted with one or more substituents, preferably 1 to 4 substituents, more preferably 1 to 2 substitutents, at any available point of attachment on the straight and/or branched chain. Exemplary substituents may include but are not limited to one or more of halogen, haloalkyl (e.g., a single halo substituent or multiple halo substitutents forming, in the latter case, groups such as a perfluoroalkyl group including for example, —$CHCl_2$ and/or $CF_3$), haloalkoxyl (e.g., including trifluoromethoxy), cyano, nitro, alkenyl, alkynyl, cycloalkyl, heterocycle, heteroaryl, aryl, $OR_a$, $SR_a$, $S(=O)R_e$, $S(=O)_2R_e$, $P(=O)_2R_e$, $S(=O)_2OR_e$, $P(=O)_2OR_e$, $P(=O)(OR)_2$, $NR_bR_c$, $NR_bS(=O)_2R_e$, $NR_bP(=O)_2R_e$, $S(=O)_2NR_bR_c$, $P(=O)_2NR_bR_c$, $C(=O)OR_a$, $C(=O)R_a$, $C(=O)NR_bR_c$, $OC(=O)R_a$, $C(=O)ONR_bR_c$, $OC(=O)NR_bR_c$, $NR_bC(=O)OR_a$, $NR_dC(=O)NR_bR_c$, $NR_dS(=O)_2NR_bR_c$, $NR_dP(=O)_2NR_bR_e$, $NR_bC(=O)R_a$, and/or $NR_bP(=O)_2R_c$, wherein $R_a$, $R_b$, $R_c$, $R_d$ and $R_e$ are selected from hydrogen, alkyl, alkenyl, aminoalkyl, alkylaminoalkyl, cycloalkyl(alkyl), aryl(alkyl), heterocyclo(alkyl), heteroaryl(alkyl), cycloalkyl, aryl, heterocyclo, and/or heteroaryl, except $R_e$ is not hydrogen; and additionally, when $R_b$ and $R_c$ are attached to the same nitrogen atom, they may be joined together to form a cycloamino group. Each of $R_a$, $R_b$, $R_c$, $R_d$ and/or $R_e$ on the alkyl and/or cyclic moieties in turn may be optionally substituted with one to three groups, preferably substituted with up to two groups (0 to 2 groups), selected from lower alkyl, lower alkenyl, $R_f$ and a lower alkyl or lower alkenyl substituted with one to two $R_f$, wherein $R_f$ is selected from one or more of cyano, halogen, halo$C_1$-$C_4$alkyl, halo$C_1$-$C_4$alkoxy, keto (=O) (where valence allows), nitro, —OH, —O($C_1$-$C_4$alkyl), —SH, —S($C_1$-$C_4$alkyl), —S(=O)($C_1$-$C_4$alkyl), —S(=O)$_2$($C_1$-$C_4$alkyl), —$NH_2$, —NH($C_1$-$C_4$alkyl), —N($C_1$-$C_4$alkyl)$_2$, —NH(cycloalkyl), —NH(phenyl), phenyl, benzyl, phenoxy, benzyloxy, —NHS(=O)$_2$($C_1$-$C_4$alkyl), —S(=O)$_2$NH$_2$, —S(=O)$_2$NH($C_1$-$C_4$alkyl), —S(=O)$_2$N($C_1$-$C_4$alkyl)$_2$, —S(=O)$_2$NH(cycloalkyl), —S(=O)$_2$NH(phenyl), —C(=O)OH, —C(=O)O($C_1$-$C_4$alkyl), —C(=O)H, —C(=O)($C_1$-$C_4$alkyl), —C(=O)NH$_2$, —C(=O)NH($C_1$-$C_4$alkyl), —C(=O)N($C_1$-$C_4$alkyl)$_2$, —C(=O)NH(cycloalkyl), —C(=O)NH(phenyl), —C(=O)ONH$_2$, —C(=O)ONH($C_1$-$C_4$alkyl), —C(=O)ON($C_1$-$C_4$alkyl)$_2$, —C(=O)ONH(cycloalkyl), —C(=O)ONH(phenyl), —NHC(=O)O$C_1$-$C_4$alkyl, —N($C_1$-$C_4$alkyl)C(=O)O($C_1$-$C_4$alkyl), —NHC(=O)NH$_2$, —NHC(=O)NH($C_1$-$C_4$alkyl), —NHC(=O)N($C_1$-$C_4$alkyl)$_2$, —NHC(=O)NH(cycloalkyl), —NHC(=O)NH(phenyl), —NHC(=O)H, and/or —NHC(=O)($C_1$-$C_4$alkyl).

The term "alkenyl" refers to a straight or branched chain hydrocarbon radical containing from 2 to 12 carbon atoms and at least one carbon-carbon double bond. Exemplary such groups include ethenyl and propenyl (allyl). Lower alkenyl means an alkenyl group of 2 to 4 carbon atoms. "Substituted alkenyl" refers to an alkenyl group substituted with one or more substituents, preferably 1 to 4 substituents, more preferably 1 to 2 substituents, at any available point of attachment. Exemplary substituents may include, but are not limited to, alkyl, substituted alkyl, and those groups recited above as exemplary substituents for substituted alkyl groups.

The term "alkynyl" refers to a straight or branched chain hydrocarbon radical containing from 2 to 12 carbon atoms and at least one carbon-to-carbon triple bond. Exemplary such groups include ethynyl. "Substituted alkynyl" refers to an alkynyl group substituted with one or more substituents, preferably 1 to 4 substituents, more preferably 1 to 2 substituents, at any available point of attachment. Exemplary substituents include, but are not limited to, alkyl, substituted alkyl, and those groups recited above as exemplary substituents for substituted alkyl groups.

The term "alkoxy" refers to the group $OR_g$, wherein $R_g$ is selected from alkyl, alkenyl, and cycloalkyl. Thus, a $C_1$-$C_4$alkoxy is an alkoxy group $OR_{g'}$ wherein $R_{g'}$ is a $C_1$-$C_4$alkyl, $C_2$-$C_4$alkenyl or $C_3$-$C_4$cycloalkyl. A substituted alkoxy group is an alkoxy group as defined above wherein at least one of the alkyl, alkenyl, and/or cycloalkyl moieties is substituted with one or more, preferably 1 to 4, more preferably 1 to 2, groups selected from those recited herein for the named moiety, e.g., for substituted alkyl, alkenyl and cycloalkyl groups, respectively.

The term "amino" refers to NH₂, and an alkylamino refers to an amino group wherein one or both of the hydrogen atoms is (or are), replaced with a group chosen from alkyl, alkenyl, and/or cycloalkyl. Thus, alkylamino means the group $NR_hR_i$, wherein $R_h$ and $R_i$ are selected from hydrogen, alkyl, alkenyl, and/or cycloalkyl, provided $R_h$ and $R_i$ are not both hydrogen. "Aminoalkyl" refers to an alkyl group as defined above substituted with an amino group, and an "alkylaminoalkyl" refers to an alkyl group as defined above substituted with one or more alkylamino groups. A substituted alkylamino group is an alkylamino group wherein at least one of the alkyl, alkenyl, and/or cycloalkyl moieties is substituted with one or more, preferably 1 to 4, more preferably 1 to 2, groups selected from those recited herein as appropriate for the recited moeity. Thus, for example, an optionally-substituted alkylamino group refers to the group —$NR_jR_k$, wherein $R_j$ and $R_k$ are selected from hydrogen, alkyl, substituted alkyl, alkenyl, substituted alkenyl, cycloalkyl, and substituted cycloalkyl, except $R_j$ and $R_k$ are not both hydrogen.

A cycloamino group refers to a group —$NR_lR_m$, wherein $R_l$ and $R_m$ join to form a monocyclic heterocyclo ring, such as, for example, N-morpholinyl, N-piperidinyl, N-piperazinyl and the like. A "substituted cycloamino" is a cycloamino group having one or more, preferably 1 to 4, more preferably 1 to 2, substituents selected from those recited below for substituted heterocyclo groups.

The term "alkylthio" refers to the group $SR_g$, wherein $R_g$ is selected from alkyl, alkenyl, and cycloalkyl. A $C_1$-$C_4$alkylthio is an alkylthio group $SR_{g'}$ wherein $R_{g'}$ is a $C_1$-$C_4$alkyl, $C_2$-$C_4$alkenyl, or $C_3$-$C_4$cycloalkyl. A substituted alkylthio group is an alkylthio group wherein at least one of the alkyl, alkenyl, and/or cycloalkyl moieties is substituted with one or more, preferably 1 to 4, more preferably 1 to 2, groups selected from those recited herein for the named moiety.

The term "aryl" refers to monocyclic, bicyclic, and tricyclic aromatic hydrocarbon groups which have at least 1 to 2 aromatic rings, including phenyl and naphthyl. The aryl group may have fused thereto a second or third ring which is a heterocyclo, cycloalkyl, or heteroaryl ring, provided in that case the point of attachment will be to the aryl portion of the ring system. Thus, as an illustration, exemplary aryl groups may include, without limitation,

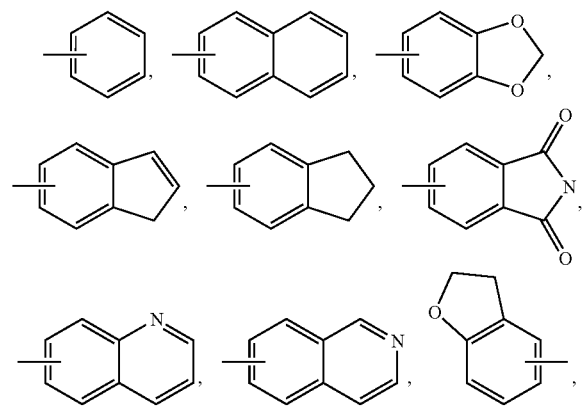

-continued

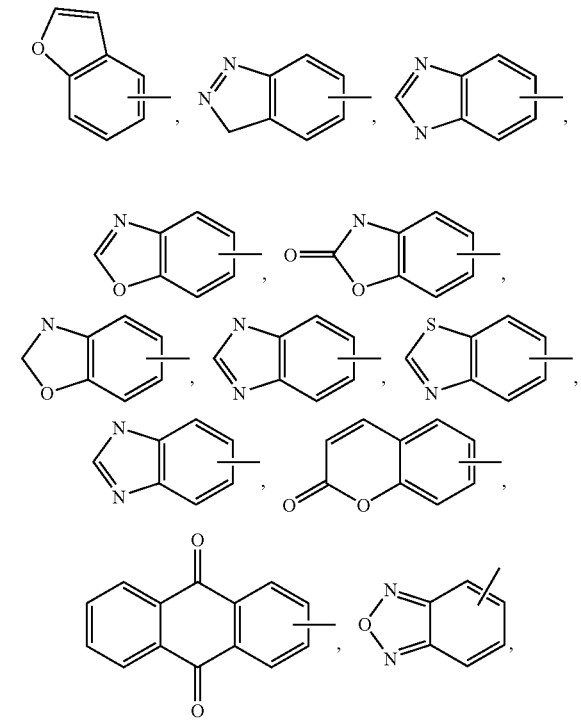

and so forth.

"Substituted aryl" refers to an aryl group substituted by one or more substituents, preferably 1 to 3 substituents, more preferably 1 to 2 substituents, at any point of attachment of the aryl ring or ring system (e.g., including any further ring fused thereto). Exemplary substituents include, but are not limited to, alkyl, substituted alkyl, and where valence allows those groups recited above as exemplary substituents for substituted alkyl groups.

The term "cycloalkyl" refers to a fully saturated and partially unsaturated cyclic hydrocarbon group containing from 1 to 3 rings and 3 to 8 carbons per ring. Exemplary such groups include cyclopropyl, cyclobutyl, cyclopentyl, cyclohexyl, cycloheptyl, cyclobutenyl, cyclopentenyl, cyclohexenyl, etc. A cycloalkyl ring may have a carbon ring atom replaced with a carbonyl group (C=O), as illustrated below. Cycloalkyl groups include such rings having a second or third ring fused thereto that is a heterocyclo, heteroaryl, or aryl group, provided that in such cases the point of attachment is to the cycloalkyl portion of the ring system. The term "cycloalkyl" also includes such rings having a second or third ring attached to the ring or ring system in a spiro fashion wherein the spiro ring is either a heterocyclo or carbocyclic ring. "Substituted cycloalkyl" refers to a cycloalkyl group as defined above having one or more substituents, preferably 1 to 4 substituents, more preferably 1 to 2 substituents, at any available point of attachment on the cycloalkyl ring or ring system (including any rings fused or attached thereto). Exemplary substituents include, but are not limited to, alkyl, substituted alkyl, and where valence allows those groups recited above as exemplary substituents for substituted alkyl groups.

Thus, as an illustration non-limiting examples of cycloalkyl rings may include,

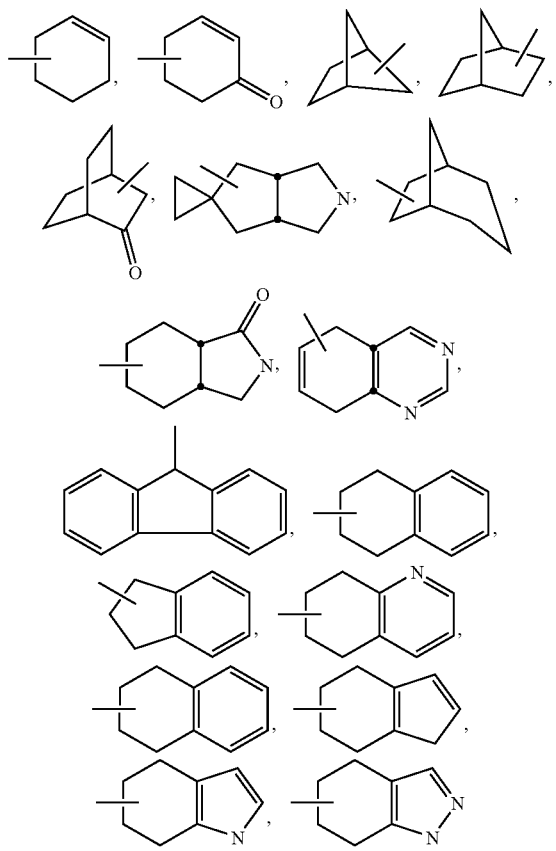

and the like.

The terms "heterocycle," "heterocyclic" and "heterocyclo" refer to fully saturated or partially unsaturated non-aromatic cyclic groups (for example, 4 to 7 membered monocyclic, 7 to 11 membered bicyclic, or 10 to 16 membered tricyclic ring systems) which have at least one heteroatom in at least one carbon atom-containing ring. Each ring of the heterocyclic group containing a heteroatom may have 1, 2, 3, or 4 heteroatoms selected from nitrogen atoms, oxygen atoms and/or sulfur atoms, where the nitrogen and/or sulfur heteroatoms may optionally be oxidized and the nitrogen heteroatoms may optionally be quaternized. A heterocyclo ring may have a carbon ring atom replaced with a carbonyl group (C=O), as illustrated above for cycloalkyl groups. The heterocyclic group may be attached to the remainder of the molecule at any nitrogen atom or carbon atom of the ring or ring system. Additionally, the heterocyclo group may have a second or third ring attached thereto in a spiro or fused fashion, provided the point of attachment is to the heterocyclo group. An attached spiro ring may be a carbocyclic or heterocyclic ring, and the second and/or third fused ring may be a cycloalkyl, aryl or heteroaryl ring.

Exemplary monocyclic heterocyclic groups include azetidinyl, pyrrolidinyl, pyrrolinyl, pyrazolidinyl, pyrazolinyl, imidazolidinyl, oxazolidinyl, piperidinyl, piperazinyl, morpholinyl, tetrahydrofuryl, tetrahydropyranyl, thiamorpholinyl, and the like.

Exemplary bicyclic heterocyclic groups may include indolinyl, isoindolinyl, quinuclidinyl, benzopyrrolidinyl, benzopyrazolinyl, benzoimidazolidinyl, benzopiperidinyl, benzopiperazinyl, tetrahydroisoquinolinyl, tetrahydroquinolinyl, dihydroisoindolyl and the like.

"Substituted heterocycle," "substituted heterocyclic," and "substituted heterocyclo" refer to heterocycle, heterocyclic or heterocyclo groups substituted with one or more substituents, preferably 1 to 4 substituents, more preferably 1 to 2 substituents, at any available point of attachment to the heterocyclo ring or ring system (e.g., including any ring fused or attached thereto). Exemplary substituents include, but are not limited to, alkyl, substituted alkyl, and where valence allows those groups recited above as exemplary substituents for substituted alkyl groups.

The term "heteroaryl" refers to aromatic cyclic groups (for example, 5 to 6 membered monocyclic, 7 to 11 membered bicyclic, or 10 to 16 membered tricyclic ring systems) which have at least one heteroatom in at least one carbon atom-containing ring. Each ring of the heteroaryl group containing a heteroatom may have 1, 2, 3, or 4 heteroatoms selected from nitrogen atoms, oxygen atoms and/or sulfur atoms, where the nitrogen and/or sulfur heteroatoms may optionally be oxidized and the nitrogen heteroatoms may optionally be quaternized. (The term "heteroarylium" refers to a heteroaryl group bearing a quaternary nitrogen atom and thus a positive charge.) The heteroaryl group may be attached to the remainder of the molecule at any nitrogen atom or carbon atom of the ring or ring system. Additionally, the heteroaryl group may have a second or third heterocyclic or carbocyclic (cycloalkyl or aryl) ring fused thereto provided the point of attachment is to the heteroaryl group.

Exemplary monocyclic heteroaryl groups include pyrazolyl, imidazolyl, triazolyl, furyl, thienyl, oxazolyl, isoxazolyl, thiazolyl, pyrrolyl, pyridyl, pyridazinyl, pyrimidinyl, pyrazinyl, triazinyl (s, as, or v), and the like. Unless reference is made to a specific point of attachment, e.g., as in pyrid-2-yl, pyridazin-3-yl, it is intended that such heteroaryl groups can be bonded to another moiety at any available point of attachment.

Exemplary bicyclic heteroaryl groups include benzothiazolyl, benzoxazolyl, benzoxadiazolyl, benzothienyl, quinolinyl, quinazolinyl, purinyl, chromenyl, indolyl, indazolyl, isoquinolinyl, benzimidazolyl, benzopyranyl, benzofuryl, isobenzofuryl, benzopyranyl, cinnolinyl, quinoxalinyl, pyrrolopyridyl, furopyridinyl (such as furo[2,3-c]pyridinyl, furo[3,2-b]pyridinyl] or furo[2,3-b]pyridinyl), phthalazinyl, naphthyridinyl, triazinylazepinyl, and the like.

"Substituted heteroaryl" refers to heteroaryl groups substituted with one or more substituents as valence allows, preferably 1 to 3 substituents, more preferably 1 to 2 substituents, at any available point of attachment to the heteroaryl ring or ring system (including any further ring fused thereto). Exemplary substituents include, but are not limited to, alkyl, substituted alkyl, and where valence allows those groups recited above as exemplary substituents for substituted alkyl groups.

When reference is made to an optionally-substituted, specifically-named aryl, heteroaryl, cycloalkyl, or heterocyclo ring, the optional substituents may be selected as valence allows from the groups recited above for the genus of rings of which the specifically-named group is a member. For example, "optionally-substituted phenyl" includes unsubstituted phenyl rings as well as phenyl rings containing one or more substituents selected from those recited above for aryl groups. "Optionally-substituted pyridyl, pyridazinyl, pyrimidinyl, and pyrazinyl," includes unsubstituted pyridyl, pyridazinyl, pyrimidinyl, and pyrazinyl rings, as well as such rings containing one or more substituents selected from those recited above for heteroaryl groups.

The term "optionally substituted oxadiazolyl" as used herein is intended to refer to the group,

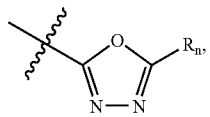

wherein $R_n$ is selected from a substituent recited above for substituted heteroaryl groups.

The term "quaternary nitrogen" refers to a tetravalent positively charged nitrogen atom including, for example, the positively charged nitrogen in a tetraalkylammonium group (e.g., tetramethylammonium, N-methylpyridinium), the positively charged nitrogen in protonated ammonium species (e.g., trimethyl-hydroammonium, N-hydropyridinium), the positively charged nitrogen in amine N-oxides (e.g., N-methyl-morpholine-N-oxide, pyridine-N-oxide), and the positively charged nitrogen in an N-amino-ammonium group (e.g., N-aminopyridinium).

The terms "halogen" or "halo" refer to chlorine, bromine, fluorine and/or iodine.

The term "haloalkyl" refers to an alkyl group having a single halo substituent or multiple halo substitutents forming, for example, groups such as perfluoroalkyl including trichloromethyl or trifluoromethyl ($CCl_3$ or $CF_3$). A halo$C_1$-$C_4$alkyl refers to a $C_1$-$C_4$alkyl having one or more halo substituents.

The term "haloalkoxy" refers to the group —$OR_p$, wherein $R_p$ is a haloalkyl as defined immediately above, thus forming, for example, groups such —$OCCl_3$ or —$OCF_3$. A halo$C_1$-$C_4$alkoxy refers to a $C_1$-$C_4$alkoxy having one or more halo substituents.

The term "unsaturated" when used herein is intended to refer to fully unsaturated and partially unsaturated moieties.

When a functional group is termed "protected", this means that the group is in modified form to mitigate, especially preclude, undesired side reactions at the protected site. Suitable protecting groups for the methods and compounds described herein include, without limitation, those described in standard textbooks, such as Greene & Wuts, *Protective Groups in Organic Synthesis,* Wiley, N.Y. (1999).

The term "selective" as used herein with reference to the capability of the claimed compounds to inhibit p38 activity means that the compound in question has a level of activity as measured in enzyme assays for inhibiting the p38 α/β kinase that is significantly greater than the activity of the compound in inhibiting a plurality of other kinases falling within families throughout the human kinome. A suitable standard for the term "significantly greater activity" is that the activity of the compound has about 500-fold or more greater activity for inhibiting p38α/β enzyme as compared with the activity of the compound in inhibiting other kinases, for example, as compared with the activity of the compound in inhibiting about twenty-five or more other kinases, in another example, as compared with about fifty or more other kinases, and in yet another example, as compared with about 100 or more other kinases. Thus, a selective p38 inhibitor as defined herein according to one embodiment will inhibit the α-isoform of the p38 kinase, the β-isoform of the p38 kinase, and/or both the α and β forms of the p38 kinase, at least 500 times greater than it will inhibit any one of a plurality of other kinases. Reference to "other kinases" herein is intended to include kinases known in the field other than the p38 α/β kinases. For example, various known kinases and kinase families other than the 38 α/β kinase are identified in WO 02/062804, and in Manning, G. et al., *The Protein Kinase Complement of the Human Genome,* Science (Washington, D.C., United States) (2002), 298(5600), at pp. 1912-1916, 1933-1934, which is incorporated herein by reference. "Other kinases" as idenfitied therein thus may include, without limitation, one or more kinases chosen from the following kinases and/or kinase families: CaMK1, CaMK2, CDK, DAPK, EMT, FGF, FMS, GSK3, LCK, PDGF-R, PKA, PCK, RAF, RIPK, LIMK-1, SYK, Met, PAK-4, PAK-5, ZC-1, STLK-2, DDR-2, Aurora 1, Aurora 2, Bub-1, PLK, Chk1, Chk2, HER2, JAK, raf1, MEK1, EGF-R, RSK/RSK, IGF-R, IRAK, VEGF-R, P13K, PDK, HIPK, STKR, BRD, Wnk, NKF3, NKF4, NKF5, weel kinase, Src, Abl, ILK, MK-2, IKK-2, RIPK, Cdc7, Ste11, Ste20, Ste7, Tec, Trk, and/or Nek, and so forth. The above is an exemplary, non-limiting list of other kinases. Manning identified 518 protein kinases, and applicant intends to incorporate each one of these 518 protein kinases other than the p38 kinase in the definition of the term "other kinases" as used herein.

There are many enzyme assays known in the field that may be used to measure the levels of activity to determine selectivity. Applicant has described certain enzyme assays below but does not intend to be limited to use of these specific assays with regard to the definition of selectivity herein.

Unless otherwise indicated, a heteroatom with an unsatisfied valence is understood to have hydrogen atoms sufficient to satisfy the valences, as one skilled in the field will appreciate.

The compounds of formula I may form salts which are also within the scope of this invention. Reference to a compound of the formula I herein is understood to include reference to salts thereof, unless otherwise indicated. The term "salt(s)", as employed herein, denotes acidic and/or basic salts formed with inorganic and/or organic acids and bases. In addition, when a compound of formula I contains both a basic moiety, such as but not limited to a pyridine or imidazole, and an acidic moiety such as but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts may also be useful, e.g., in isolation or purification steps which may be employed during preparation. Salts of the compounds of the formula I may be formed, for example, by reacting a compound I with an amount of acid or base, such as an equivalent amount, in a medium such as one in which the salt precipitates or in an aqueous medium followed by lyophilization.

The compounds of formula I which contain a basic moiety, such as but not limited to an amine or a pyridine or imidazole ring, may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, hydroxyethanesulfonates (e.g., 2-hydroxyethanesulfonates), lactates, maleates, methanesulfonates, naphthalenesulfonates (e.g., 2-naphthalenesulfonates), nicotinates, nitrates, oxalates, pectinates, persulfates, phenylpropionates (e.g., 3-phenylpropionates), phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The compounds of formula I which contain an acidic moiety, such as but not limited to a carboxylic acid, may form salts with a variety of organic and inorganic bases. Exemplary basic salts include ammonium salts, alkali metal salts such as sodium, lithium and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glycamides, t-butyl amines, and salts with amino acids such as arginine, lysine and the like. Basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

Prodrugs and solvates of the compounds of the invention are also contemplated herein. The term "prodrug" as employed herein denotes a compound which, upon administration to a subject, undergoes chemical conversion by metabolic or chemical processes to yield a compound of the formula I, or a salt and/or solvate thereof. Solvates of the compounds of formula I include, for example, hydrates. Methods of solvation are known in the art.

Any compound that will be converted in vivo to provide the bioactive agent (i.e., a compound of formula I) is a prodrug within the scope and spirit of the invention. For example, pro-drug compounds of formula I may be soluble ester moieties (see, e.g., J. Med. Chem. 2004, at pp. 2393-2404), phosphates and/or alkylphosphates (see, e.g. WO 03/080047), and/or moieties as described in one or more of the following references:

a) *Design of Prodrugs,* edited by H. Bundgaard, (Elsevier, 1985), and *Methods in Enzymology,* Vol. 112, at pp. 309-396, edited by K. Widder, et al. (Academic Press, 1985);

b) *A Textbook of Drug Design and Development,* edited by Krosgaard-Larsen and H. Bundgaard, Chapter 5, *"Design and Application of Prodrugs,"* by H. Bundgaard, at pp. 113-191 (1991);

c) H. Bundgaard, *Advanced Drug Delivery Reviews,* Vol. 8, pp. 1-38 (1992);

d) H. Bundgaard, et al., *Journal of Pharmaceutical Sciences,* Vol. 77, p. 285 (1988); and e) N. Kakeya, et al., *Chem. Pharm. Bull.,* Vol. 32, p. 692 (1984).

Advantageously, in one embodiment the compounds of formula I herein include an amide and the prodrug is incorporated onto the amide portion of the molecule.

Compounds of the formula I, and salts or prodrugs thereof, may exist in their tautomeric form (for example, as an amide or imino ether). All such tautomeric forms are contemplated herein as part of the present invention.

All stereoisomers of the present compounds (for example, those which may exist due to asymmetric carbons on various substituents), including enantiomeric forms and diastereomeric forms, are contemplated within the scope of this invention. Individual stereoisomers of the compounds of the invention may, for example, be substantially free of other isomers (e.g., as a pure or substantially pure optical isomer having a specified activity), or may be admixed, for example, as racemates or with all other, or other selected, stereoisomers. The chiral centers of the present invention may have the S or R configuration as defined by the IUPAC 1974 Recommendations. The racemic forms can be resolved by physical methods, such as, for example, fractional crystallization, separation or crystallization of diastereomeric derivatives or separation by chiral column chromatography. The individual optical isomers can be obtained from the racemates by any suitable method, including without limitation, conventional methods, such as, for example, salt formation with an optically active acid followed by crystallization.

All configurational isomers of the compounds of the present invention are contemplated, either in admixture or in pure or substantially pure form. The definition of compounds of the present invention embraces both cis (Z) and trans (E) isomers, including cis and trans isomers of cyclic hydrocarbon or heterocyclo rings.

When reference is made herein to a compound of formula (I) herein, this is intended to refer to each compound of formula (I), and each salt, prodrug, solvate, or isomer thereof, alone or in combination with other matter, without limitation to the manner in which said compound of formula (I), or salt, prodrug, solvate, or isomer thereof, is made or formed. Thus, for example, the compound of formula (I), or salt, prodrug, solvate or isomer thereof, may be present in a pure form, isolated form, crude form, liquid or solid form, and may optionally be existing in the presence of other compounds not of formula (I), e.g., together with one or more excipients or impurities, in a pharmaceutical preparation before administration to a patient, as formed in the body of a patient after administration to a patient (thus existing together with other biological matter), and so forth.

Throughout the specification, groups and substituents thereof may be chosen to provide stable moieties and compounds.

The term "base" when used to describe the reaction conditions for making compounds of formula (I) herein, and/or for making intermediates or precursors to compounds of formula (I), is intended to include metal oxides, hydroxides or alkoxides, hydrides, or compounds such as ammonia, that accept protons in water or solvent. Thus, exemplary bases include, but are not limited to, alkali metal hydroxides and alkoxides (i.e., $MOR_q$, wherein M is an alkali metal such as potassium, lithium, or sodium, and $R_q$ is hydrogen or alkyl, as defined above, more preferably where R is straight or branched chain $C_{1-5}$ alkyl, thus including, without limitation, potassium hydroxide, potassium tert-butoxide, potassium tert-pentoxide, sodium hydroxide, sodium tert-butoxide, lithium hydroxide, etc.); other hydroxides such as magnesium hydroxide ($Mg(OH)_2$) or calcium hydroxide ($Ca(OH)_2$); alkali metal hydrides (i.e., MH, wherein M is as defined above, thus including, without limitation, sodium hydride and lithium hydride); alkylated disilazides, such as, for example, potassium hexamethyldisilazide and lithium hexamethyldisilazide; carbonates such as potassium carbonate ($K_2CO_3$), sodium carbonate ($Na_2CO_3$), potassium bicarbonate ($KHCO_3$), and sodium bicarbonate ($NaHCO_3$), alkyl ammonium hydroxides such as n-tetrabutyl ammonium hydroxide (TBAH); and so forth.

The term "coupling agent" when used herein refers to a reagent or combination of reagents designed to speed up the coupling process and inhibit side reactions. Thus, for example, the term "coupling agent" may include a coupling additive, such as CDI, HOBt, HOAt, HODhbt, HOSu, or NEPIS, used in combination with another coupling reagent. Particular peptide-coupling reagents may include DCC, EDC, BBC, BDMP, BOMI, HATU, HAPyU, HBTU, TAPipU, AOP, BDP, BOP, PyAOP, PyBOP, TDBTU, TNTU, TPTU, TSTU, BEMT, BOP-Cl, BroP, BTFFH, CIP, EDPBT, Dpp-Cl, EEDQ, FDPP, HOTT-PF6, TOTT-BF4, PyBrop, PyClop, and TFFH. See "Peptide Coupling Reagents: Names, Acronyms and References," Albany Molecular Research, Inc., Technical Reports, Vol. 4, No. 1, incorporated herein by reference.

The terms "halogenating agent" or "halogenating reagent" may include inorganic and organic halogenating reagents. Examples of inorganic halogenating reagents include chlorine, bromine, iodine, fluorine, and sodium hypochlorite. Organic halogenting reagents include phosphorous oxychloride ($POCl_3$), chlorosuccinimide (NCS), N-bromosuccinimide (NBS), N-iodosuccinimide (NIS), 1,3-dichloro-5,5-dimethylhydantoin, 1,3-dibromo-5,5-dimethylhydantoin, and 1,3-diiodo-5,5 -dimethyihydantoin.

When reference is made to a "solvent" or "suitable solvent" in describing reaction conditions herein, it should be understood this many mean a single solvent as well as mixtures of solvents. As non-limiting examples, solvents may be selected, as appropriate for a given reaction step, from, for example, aprotic polar solvents such as DMF, DMA, DMSO, dimethylpropyleneurea, N-methylpyrrolidone, and hexamethylphosphoric triamide; ether solvents such as diethyl ether, THF, 1,4-dioxane, methyl t-butyl ether, dimethoxymethane, and ethylene glycol dimethyl ether; alcohol solvents such as MeOH, EtOH, and isopropanol; and halogen-containing solvents such as methylene chloride, chloroform, carbon tetrachloride, and 1,2-dichloroethane.

ALTERNATE EMBODIMENTS

Various alternate embodiments of the invention are contemplated. As an illustration, alternate embodiments of the compounds of the present invention may include compounds of the formula (Ia), (Ib), (Ic), and/or (Id), below, and/or pharmaceutically acceptable salts, isomers, and/or prodrugs thereof.

For example, according to one aspect of the invention, there are provided compounds having the formula (Ia):

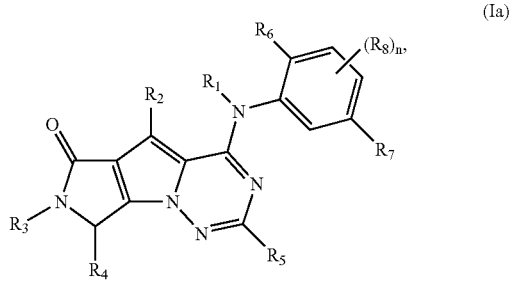

(Ia)

and/or pharmaceutically-acceptable salts, prodrugs, and/or isomers thereof, in which $R_1$, $R_2$, $R_3$, $R_4$, $R_5$, $R_6$, $R_7$, and $R_8$ are as defined above for compounds of formula (I), and n is 0 or 1.

According to another embodiment of the invention, there are provided compounds of formula (Ia), above, and/or pharmaceutically-acceptable salts, prodrugs, and/or isomers thereof, in which:

$R_1$ is hydrogen;

$R_2$ is selected from hydrogen, alkyl, substituted alkyl, alkenyl, substituted alkenyl, halogen, cyano, nitro, amino, alkylamino, hydroxy, alkoxy, substituted alkoxy, cycloalkyl, substituted cycloalkyl, aryl, substituted aryl, heterocyclo, substituted heterocyclo, heteroaryl, and substituted heteroaryl;

$R_3$ is selected from hydrogen, alkyl, substituted alkyl, alkenyl, substituted alkenyl, cycloalkyl, substituted cycloalkyl, aryl, substituted aryl, heterocyclo, substituted heterocyclo, heteroaryl, and substituted heteroaryl;

$R_4$ and $R_5$ are independently selected from hydrogen, alkyl, and substituted alkyl;

$R_6$, $R_7$ and $R_8$ are at each occurrence independently selected from alkyl, substituted alkyl, alkenyl, substituted alkenyl, halogen, cyano, —$OR_9$, —$SR_9$, —$S(=O)R_{11}$, —$S(=O)_2R_{11}$, —$S(=O)_2OR_{11}$, —$NR_9R_{10}$, —$NR_9S(=O)_2R_{11}$, —$S(=O)_2NR_9R_{10}$, —$C(=O)OR_9$, —$C(=O)R_9$, —$C(=O)NR_9R_{10}$, —$NR_9C(=O)OR_{10}$, —$NR_{12}C(=O)NR_9R_{10}$, —$NR_{12}S(=O)_2NR_9R_{10}$, —$NR_9C(=O)R_{10}$, cycloalkyl, substituted cycloalkyl, aryl, substituted aryl, heterocyclo, substituted heterocyclo, heteroaryl, and substituted heteroaryl;

$R_9$, $R_{10}$, and $R_{12}$ are independently at each occurrence selected from hydrogen, alkyl, substituted alkyl, cycloalkyl, substituted cycloalkyl, heterocycle, substituted heterocycle, aryl, substituted aryl, heteroaryl and substituted heteroaryl, or alternatively, $R_9$ and $R_{10}$ when attached to the same nitrogen atom as in —$NR_9R_{10}$ can be taken together to form a heterocyclo, heteroaryl, substituted heterocyclo, or substituted heteroaryl;

$R_{11}$ is selected from alkyl, substituted alkyl, cycloalkyl, substituted cycloalkyl, heterocycle, substituted heterocycle, aryl, substituted aryl, heteroaryl and substituted heteroaryl; and n is 0 or 1.

According to another embodiment of the invention, there are provided compounds of formula (Ia), above, and/or pharmaceutically-acceptable salts, prodrugs, and/or isomers thereof, in which:

$R_1$ is hydrogen;

$R_2$ is selected from hydrogen, lower alkyl, substituted lower alkyl, halogen, cyano, nitro, amino, alkylamino, hydroxy, lower alkoxy, and substituted lower alkoxy;

$R_3$ is selected from hydrogen, $C_{1-6}$alkyl, and substituted $C_{1-6}$alkyl;

$R_4$ is hydrogen;

$R_5$ is hydrogen;

$R_6$, $R_7$ and $R_8$ are at each occurrence independently selected from alkyl, substituted alkyl, alkenyl, substituted alkenyl, halogen, cyano, —$OR_9$, —$SR_9$, —$S(=O)R_{11}$, —$S(=O)_2R_{11}$, —$S(=O)_2OR_{11}$, —$NR_9R_{10}$, —$NR_9S(=O)_2R_{11}$, —$S(=O)_2NR_9R_{10}$, —$C(=O)OR_9$, —$C(=O)R_9$, —$C(=O)NR_9R_{10}$, —$NR_9C(=O)OR_{10}$, —$NR_{12}C(=O)NR_9R_{10}$, —$NR_{12}S(=O)_2NR_9R_{10}$, —$NR_9C(=O)R_{10}$, cycloalkyl, substituted cycloalkyl, aryl, substituted aryl, heterocyclo, substituted heterocyclo, heteroaryl, and substituted heteroaryl;

$R_9$, $R_{10}$, and $R_{12}$ are independently at each occurrence selected from hydrogen, alkyl, substituted alkyl, cycloalkyl, substituted cycloalkyl, heterocycle, substituted heterocycle, aryl, substituted aryl, heteroaryl and substituted heteroaryl, or alternatively, $R_9$ and $R_{10}$ when attached to the same nitrogen atom as in —$NR_9R_{10}$ can be taken together to form a heterocyclo, heteroaryl, substituted heterocyclo, or substituted heteroaryl;

R$_{11}$ is selected from alkyl, substituted alkyl, cycloalkyl, substituted cycloalkyl, heterocycle, substituted heterocycle, aryl, substituted aryl, heteroaryl and substituted heteroaryl; and n is 0 or 1.

According to another embodiment of the invention, there are provided compounds of formula (Ia), above, and/or pharmaceutically-acceptable salts, prodrugs, and/or isomers thereof, in which:

R$_1$ is hydrogen;

R$_2$ is selected from hydrogen, C$_{1-6}$alkyl, C$_{1-6}$alkoxy, amino, cyano, trifluoromethyl, halogen, or C$_{1-6}$alkyl substituted with one to three of halogen, amino, trifluoromethyl, hydroxy, C$_{1-6}$alkoxy, and/or cyano;

R$_3$ is selected from C$_{1-6}$alkyl, or C$_{1-6}$alkyl substituted with one to three of halogen, amino, trifluoromethyl, hydroxy, C$_{1-6}$alkoxy, cyano, phenyl and/or pyridyl, said phenyl and/or pyridyl in turn being optionally substituted with one to three of lower alkyl, halogen, cyano, trifluoromethyl and/or lower alkoxy;

R$_4$ is hydrogen;

R$_5$ is hydrogen;

R$_6$ is selected from lower alkyl and halogen;

R$_7$ is selected from alkyl, substituted alkyl, alkenyl, substituted alkenyl, halogen, cyano, —OR$_9$, —SR$_9$, —S(=O)R$_{11}$, —S(=O)$_2$R$_{11}$, —S(=O)$_2$OR$_{11}$, —NR$_9$R$_{10}$, —NR$_9$S(=O)$_2$R$_{11}$, —S(=O)$_2$NR$_9$R$_{10}$, —C(=O)OR$_9$, —C(=O)R$_9$, —C(=O)NR$_9$R$_{10}$, —NR$_9$C(=O)OR$_{10}$, —NR$_{12}$C(=O)NR$_9$R$_{10}$, —NR$_{12}$S(=O)$_2$NR$_9$R$_{10}$, —NR$_9$C(=O)R$_{10}$, cycloalkyl, substituted cycloalkyl, aryl, substituted aryl, heterocyclo, substituted heterocyclo, heteroaryl, and substituted heteroaryl;

R$_9$, R$_{10}$, and R$_{12}$ are independently at each occurrence selected from hydrogen, alkyl, substituted alkyl, cycloalkyl, substituted cycloalkyl, heterocycle, substituted heterocycle, aryl, substituted aryl, heteroaryl and substituted heteroaryl, or alternatively, R$_9$ and R$_{10}$ when attached to the same nitrogen atom as in —NR$_9$R$_{10}$ can be taken together to form a heterocyclo, heteroaryl, substituted heterocyclo, or substituted heteroaryl;

R$_{11}$ is selected from alkyl, substituted alkyl, cycloalkyl, substituted cycloalkyl, heterocycle, substituted heterocycle, aryl, substituted aryl, heteroaryl and substituted heteroaryl; and n is 0.

According to yet another aspect of the invention, there are provided compounds of formula (Ia), wherein each of the variables R$_1$, R$_2$, R$_3$, R$_4$, R$_5$, R$_6$, and n may be selected as immediately defined above, and wherein R$_7$ is —C(O)NHR$_{10}$; and R$_{10}$ is hydrogen, C$_{1-6}$alkyl, C$_{3-6}$cycloalkyl, or optionally-substituted five-membered heteroaryl.

According to another aspect of the invention, there are provided compounds having the formula (Ib), (Ib)

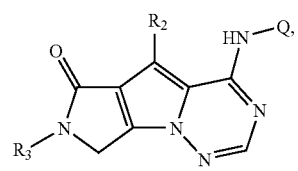

wherein Q, R$_2$, and R$_3$ are defined as in formula (I) above, and pharmaceutically-acceptable salts, isomers or prodrugs thereof.

According to another aspect of the invention, there are provided compounds having the formula (Ib), above, wherein: Q is phenyl or pyridyl optionally-substituted with up to one R$_6$ and up to one R$_7$; R$_2$ is hydrogen, C$_{1-6}$alkyl, C$_{1-6}$alkoxy, amino, cyano, trifluoromethyl, halogen, or C$_{1-6}$alkyl substituted with one to three of halogen, amino, trifluoromethyl, hydroxy, C$_{1-6}$alkoxy, and/or cyano; R$_3$ is hydrogen, C$_{1-6}$alkyl, or C$_{1-6}$alkyl substituted with one to three of halogen, amino, trifluoromethyl, hydroxy, C$_{1-6}$alkoxy, cyano, phenyl and/or pyridyl, said phenyl and/or pyridyl in turn being optionally substituted with one to three of lower alkyl, halogen, cyano, trifluoromethyl and/or lower alkoxy; and R$_6$ and R$_7$ are independently selected from alkyl, substituted alkyl, alkenyl, substituted alkenyl, halogen, cyano, —OR$_9$, —SR$_9$, —S(=O)R$_{11}$, —S(=O)$_2$R$_{11}$, —S(=O)$_2$OR$_{11}$, —NR$_9$R$_{10}$, —NR$_9$S(=O)$_2$R$_{11}$, —S(=O)$_2$NR$_9$R$_{10}$, —C(=O)OR$_9$, —C(=O)R$_9$, —C(=O)NR$_9$R$_{10}$, —NR$_9$C(=O)OR$_{10}$, —NR$_{12}$C(=O)NR$_9$R$_{10}$, —NR$_{12}$S(=O)$_2$NR$_9$R$_{10}$, —NR$_9$C(=O)R$_{10}$, cycloalkyl, substituted cycloalkyl, aryl, substituted aryl, heterocyclo, substituted heterocyclo, heteroaryl, and substituted heteroaryl; R$_9$, R$_{10}$, and R$_{12}$ are independently at each occurrence selected from hydrogen, alkyl, substituted alkyl, cycloalkyl, substituted cycloalkyl, heterocycle, substituted heterocycle, aryl, substituted aryl, heteroaryl and substituted heteroaryl, or alternatively, R$_9$ and R$_{10}$ when attached to the same nitrogen atom as in —NR$_9$R$_{10}$ can be taken together to form a heterocyclo, heteroaryl, substituted heterocyclo, or substituted heteroaryl; and R$_{11}$ is selected from alkyl, substituted alkyl, cycloalkyl, substituted cycloalkyl, heterocycle, substituted heterocycle, aryl, substituted aryl, heteroaryl and substituted heteroaryl.

According to another aspect of the invention, there are provided compounds having the formula (I) and/or formula the (Ib), above, in which Q is

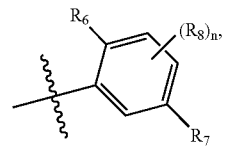

wherein R$_6$, R$_7$ and R$_8$ are as defined herein for compounds of formula (I), and n is 0 or 1.

According to another aspect of the invention, there are provided compounds having the formula (I) and/or (Ib), above, in which Q is

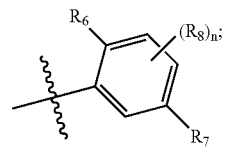

R$_6$ and R$_8$ are independently selected from lower alkyl, halogen, cyano, trifluoromethyl, lower alkoxy, and/or trifluoromethoxy; R$_7$ is —C(O)NHR$_{10}$; R$_{10}$ is hydrogen, C$_{1-6}$alkyl, C$_{3-6}$cycloalkyl, or optionally-substituted five-membered heteroaryl; and n is 0 or 1; and/or pharmaceutically-acceptable salts, prodrugs, and/or isomers thereof.

According to another aspect of the invention, there are provided compounds having the formula (Ic):

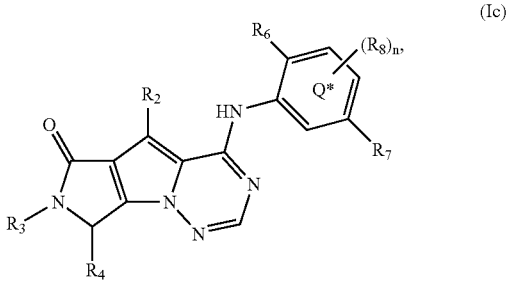

wherein each of $R_2$, $R_3$, $R_4$, $R_6$, $R_7$ and $R_8$ are as defined above for compounds of formula (I), n is 0 or 1, and Q* is phenyl or pyridyl.

According to another aspect of the invention, there are provided compounds having the formula (Ic), above, in which Q is phenyl; $R_2$ is hydrogen, $C_{1-6}$alkyl, $C_{1-6}$alkoxy, amino, cyano, trifluoromethyl, halogen, or $C_{1-6}$alkyl substituted with one to three of halogen, amino, trifluoromethyl, hydroxy, $C_{1-6}$alkoxy, and/or cyano; $R_3$ is hydrogen, $C_{1-6}$alkyl, or $C_{1-6}$alkyl substituted with one to three of halogen, amino, trifluoromethyl, hydroxy, $C_{1-6}$alkoxy, cyano, phenyl and/or pyridyl, said phenyl and/or pyridyl in turn being optionally substituted with one to three of lower alkyl, halogen, cyano, trifluoromethyl and/or lower alkoxy; $R_4$ is hydrogen; $R_6$ is halogen or lower alkyl; $R_7$ is independently selected from alkyl, substituted alkyl, alkenyl, substituted alkenyl, halogen, cyano, —$OR_9$, —$SR_9$, —$S(=O)R_{11}$, —$S(=O)_2R_{11}$, —$S(=O)_2OR_{11}$, —$NR_9R_{10}$, —$NR_9S(=O)_2R_{11}$, —$S(=O)_2NR_9R_{10}$, —$C(=O)OR_9$, —$C(=O)R_9$, —$C(=O)NR_9R_{10}$, —$NR_9C(=O)OR_{10}$, —$NR_{12}C(=O)NR_9R_{10}$, —$NR_{12}S(=O)_2NR_9R_{10}$, —$NR_9C(=O)R_{10}$, cycloalkyl, substituted cycloalkyl, aryl, substituted aryl, heterocyclo, substituted heterocyclo, heteroaryl, and/or substituted heteroaryl; $R_9$, $R_{10}$, and $R_{12}$ are independently at each occurrence selected from hydrogen, alkyl, substituted alkyl, cycloalkyl, substituted cycloalkyl, heterocycle, substituted heterocycle, aryl, substituted aryl, heteroaryl and/or substituted heteroaryl, or alternatively, $R_9$ and $R_{10}$ when attached to the same nitrogen atom as in —$NR_9R_{10}$ can be taken together to form a heterocyclo, heteroaryl, substituted heterocyclo, or substituted heteroaryl; $R_{11}$ is selected from alkyl, substituted alkyl, cycloalkyl, substituted cycloalkyl, heterocycle, substituted heterocycle, aryl, substituted aryl, heteroaryl and substituted heteroaryl; and n is 0.

Also provided are compounds having the formula (Id),

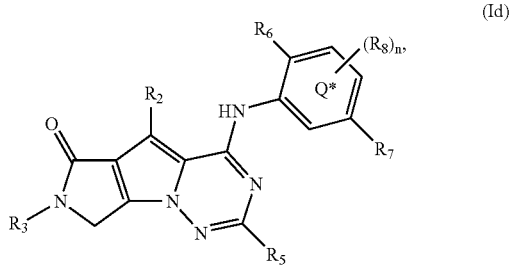

and/or pharmaceutically-acceptable salts, prodrugs, and/or isomers thereof, wherein, Q* is phenyl or pyridyl;

$R_2$ is selected from hydrogen, alkyl, substituted alkyl, alkenyl, substituted alkenyl, halogen, cyano, nitro, amino, alkylamino, hydroxy, alkoxy, substituted alkoxy, cycloalkyl, substituted cycloalkyl, aryl, substituted aryl, heterocyclo, substituted heterocyclo, heteroaryl, and substituted heteroaryl;

$R_3$ and $R_5$ are independently selected from hydrogen, alkyl, substituted alkyl, alkenyl, substituted alkenyl, cycloalkyl, substituted cycloalkyl, aryl, substituted aryl, heterocyclo, substituted heterocyclo, heteroaryl, and substituted heteroaryl;

$R_6$, $R_7$ and $R_8$ are at each occurrence independently selected from alkyl, substituted alkyl, alkenyl, substituted alkenyl, halogen, cyano, —$OR_9$, —$SR_9$, —$S(=O)R_{11}$, —$S(=O)_2R_{11}$, —$S(=O)_2OR_{11}$, —$NR_9R_{10}$, —$NR_9S(=O)_2R_{11}$, —$S(=O)_2NR_9R_{10}$, —$C(=O)OR_9$, —$C(=O)R_9$, —$C(=O)NR_9R_{10}$, —$NR_9C(=O)OR_{10}$, —$NR_{12}C(=O)NR_9R_{10}$, —$NR_{12}S(=O)_2NR_9R_{10}$, —$NR_9C(=O)R_{10}$, cycloalkyl, substituted cycloalkyl, aryl, substituted aryl, heterocyclo, substituted heterocyclo, heteroaryl, and substituted heteroaryl;

$R_9$, $R_{10}$, and $R_{12}$ are independently at each occurrence selected from hydrogen, alkyl, substituted alkyl, cycloalkyl, substituted cycloalkyl, heterocycle, substituted heterocycle, aryl, substituted aryl, heteroaryl and substituted heteroaryl, or alternatively, $R_9$ and $R_{10}$ when attached to the same nitrogen atom as in —$NR_9R_{10}$ can be taken together to form a heterocyclo, heteroaryl, substituted heterocyclo, or substituted heteroaryl;

$R_{11}$ is selected from alkyl, substituted alkyl, cycloalkyl, substituted cycloalkyl, heterocycle, substituted heterocycle, aryl, substituted aryl, heteroaryl and substituted heteroaryl; and n is 0 or 1.

According to another aspect of the invention, there are provided compounds of formula (Id), wherein Q is phenyl; $R_2$ and $R_5$ are selected from $C_{1-4}$alkyl or $C_{1-4}$alkyl substituted with one to two of halogen, amino, trifluoromethyl, hydroxy, $C_{1-6}$alkoxy, and/or cyano; $R_3$ is selected from $C_{1-6}$alkyl or $C_{1-6}$alkyl substituted with one to two of halogen, amino, trifluoromethyl, hydroxy, $C_{1-6}$alkoxy, cyano, phenyl and/or pyridyl, said phenyl and/or pyridyl in turn being optionally substituted with one, two or three of lower alkyl, halogen, cyano, trifluoromethyl and/or lower alkoxy; $R_6$ is methyl or halogen; $R_7$ is alkyl, substituted alkyl, —$C(=O)NHR_{10}$, heteroaryl, or substituted heteroaryl; and $R_{10}$ is hydrogen, $C_{1-6}$alkyl, $C_{3-6}$cycloalkyl, or optionally-substituted five-membered heteroaryl; and/or pharmaceutically-acceptable salts, prodrugs, and/or isomers thereof.

According to yet another aspect of the invention, there are provided compounds of formula (Id), whereineach of the variables may be selected as immediately defined above, except $R_7$ is —C(O)$NHR_{10}$; and $R_{10}$ is $C_{1-6}$alkyl or $C_{3-6}$cycloalkyl.

In each of compounds of formulae (I) and/or (Ia), preferably $R_1$ is hydrogen or methyl, more preferably $R_1$ is hydrogen.

In each of compounds of formulae (I), (Ia), (Ib), (Ic), and/or (Id), preferably $R_2$ is selected from hydrogen, alkyl, substituted alkyl, alkenyl, substituted alkenyl, halogen, cyano, nitro, amino, alkylamino, hydroxy, alkoxy, and substituted alkoxy; more preferably $R_2$ is selected from alkyl, substituted alkyl, alkenyl, substituted alkenyl, halogen, cyano, nitro, amino, alkylamino, hydroxy, alkoxy, and substituted alkoxy; further preferred are compounds wherein $R_2$ is $C_{1-4}$alkyl, $C_{1-4}$alkoxy, amino, cyano, halogen, or trifluoromethyl; and most preferred are compounds wherein $R_2$ is methyl.

In each of compounds of formulae (I), (Ia), (Ib), (Ic), and/or (Id), preferably $R_3$ is selected from hydrogen, $C_{1-6}$alkyl, and substituted $C_{1-6}$alkyl, more preferably from $C_{1-6}$alkyl and substituted $C_{1-6}$alkyl, and most preferably from $C_{1-4}$alkyl or $C_{1-4}$alkyl substituted with one to two of halogen, amino, trifluoromethyl, hydroxy, $C_{1-6}$alkoxy, cyano, phenyl and/or pyridyl, said phenyl and/or pyridyl in turn being optionally substituted with one to two of lower alkyl, halogen, cyano, trifluoromethyl, and/or lower alkoxy.

In each of compounds of formulae (I), (Ia), and (Ic), preferably $R_4$ is selected from hydrogen, lower alkyl, substituted lower alkyl, halogen, and cyano; more preferably $R_4$ is selected from hydrogen and lower alkyl; and most preferably $R_4$ is hydrogen.

In each of compounds of formulae (I), (Ia), and (Id), preferably $R_5$ is selected from hydrogen, lower alkyl, and substituted lower alkyl; more preferably $R_5$ is selected from hydrogen and lower alkyl; and most preferably $R_5$ is hydrogen.

In each of compounds of formulae (I), (Ia), (Ib), (Ic), and/or (Id), preferably $R_6$ is selected from lower alkyl, halogen, cyano, and trifluoromethyl; more preferably $R_6$ is selected from lower alkyl and halogen; even more preferably $R_6$ is lower alkyl; and most preferably $R_6$ is methyl.

In each of compounds of formulae (I), (Ia), (Ib), (Ic), and/or (Id) preferably $R_7$ is either —C(O)NHR$_{10}$ wherein $R_{10}$ is hydrogen, $C_{1-6}$alkyl, $C_{3-6}$cycloalkyl, and optionally substituted five-membered heteroaryl, or $R_7$ is an optionally substituted five-membered heteroaryl; and/or pharmaceutically-acceptable salts, prodrugs, and/or isomers thereof. In embodiments wherein $R_7$ or $R_{10}$ is an optionally substituted five-membered heteroaryl, preferably the heteroaryl may be selected from one of:

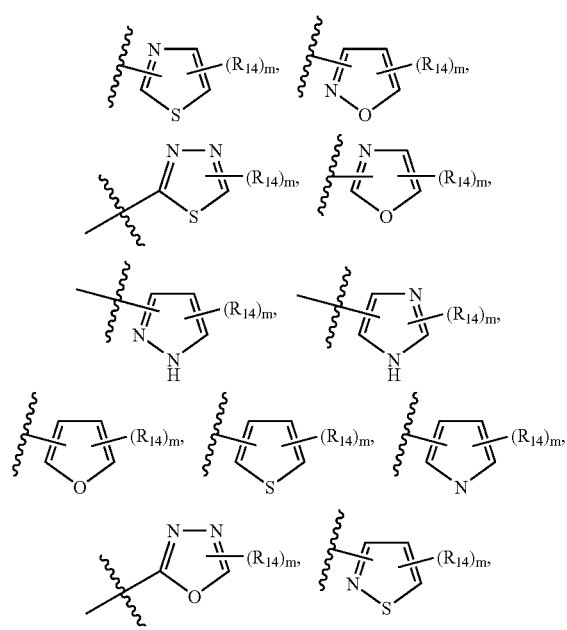

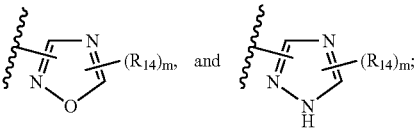

wherein m can be 0, 1, or 2 (as valence permits); and $R_{14}$ is selected from $C_{1-4}$alkyl, substituted $C_{1-4}$alkyl, trifluoromethyl, trifluoromethoxy, halogen, cyano, amino, —NH($C_{1-4}$alkyl), N($C_{1-4}$alkyl)$_2$, hydroxy, $C_{1-4}$alkoxy, thiol, alkylthio, phenyl, benzyl, phenyloxy, benzyloxy, $C_{3-7}$cycloalkyl, five-membered heteroaryl, and five to six membered heterocyclo; or as valence permits, $R_{14}$ may be taken together with one of two bonds forming a double bond of ring $R_{10}$ to form a keto (=O) group.

In certain embodiments of the invention, $R_7$ or $R_{10}$ is isoxazolyl or pyrazolyl optionally substituted with lower alkyl.

According to another aspect of the invention, compounds are provided according to formulae (I), (Ia), (Ib), (Ic), and/or (Id) wherein $R_7$ is —C(O)NHR$_{10}$ and $R_{10}$ is cyclopropyl.

According to another aspect of the invention, compounds are provided according to formulae (I), (Ia), (Ib), (Ic), and/or (Id) wherein $R_9$, $R_{10}$, and $R_{12}$ are independently at each occurrence selected from hydrogen, alkyl, substituted alkyl, cycloalkyl, heteroaryl, and substituted heteroaryl, more preferably wherein $R_9$, $R_{10}$, and $R_{12}$ are independently at each occurrence selected from hydrogen, $C_{1-6}$alkyl, substituted $C_{1-6}$alkyl, $C_{3-6}$cycloalkyl, and optionally-substituted five-membered heteroaryl, and even more preferably wherein more $R_9$, $R_{10}$, and $R_{12}$ are selected from hydrogen, $C_{1-4}$alkyl, $C_{3-6}$cycloalkyl, and optionally-substituted isoxazolyl and pyrazolyl.

According to another aspect of the invention, compounds are provided wherein $R_{11}$ is selected from alkyl and substituted alkyl, more preferably wherein $R_{11}$ is $C_{1-6}$alkyl or substituted $C_{1-6}$alkyl, and even more preferably wherein $R_{11}$ is $C_{1-4}$alkyl.

Further embodiments will be apparent to one skilled in the field upon considering the disclosure herein. For example, various alternative embodiments may be combined, and/or groups may be selected from various alternate embodiments, to arrive at further alternate embodiments, and/or groups may be selected from those recited in the claims herein, and as shown in the schemes and examples below.

Utility

The compounds of the invention are inhibitors of p38 kinase, and in particular, isoforms p38α and p38β. Accordingly, compounds of formula (I) have utility in treating conditions associated with p38 kinase activity. Such conditions include diseases or disorders in which cytokine levels are modulated as a consequence of intracellular signaling via p38, and in particular, diseases that are associated with an overproduction of cytokines IL-1, IL-4, IL-8, and TNF-α. As used herein, the terms "treating" or "treatment" encompass responsive and/or prophylaxis measures addressed to the disease state and/or its sypmtoms, e.g., measures designed to inhibit or delay the onset of the disease or disorder, achieve a full or partial reduction of the symptoms or disease state, and/or alleviate, lessen, or cure the disease and/or its symptoms. When reference is made herein to inhibition of "p-38α/β kinase," this means that either or both p38α and p38β kinase are inhibited.

In view of their activity as inhibitors of p-38α kinase, compounds of Formula (I) are useful in treating inflammatory diseases, autoimmune diseases, destructive bone disorders, proliferative disorders, angiogenic disorders, infectious diseases, neurodegenerative diseases, viral diseases, and ischemia reperfusion conditions.

More particularly, the inventive compounds may be used to treat inflammatory diseases including, but not limited to, arthritis (e.g., rheumatoid arthritis, lyme disease arthritis, osteoarthritis, traumatic arthritis, rubella arthritis, psoriatic arthritis, gouty arthritis, and other arthritic conditions); glomerulonephritis, pancreatitis (acute or chronic), diabetes, diabetic retinopathy, macular degeneration, conjunctivitis, aplastic anemia, thrombocytopenia, gastritis, chronic thyroiditis, chronic active hepatitis, multiple sclerosis, inflammatory bowel disease, ulcerative colitis, Crohn's disease, cachexia (including cachexia secondary to infection, cancer, or heart disease), periodontal disease, Alzheimer's disease, Parkinson's disease, keloid formation, pulmonary sarcoidosis, myasthenia gravis, inflammatory reaction induced by endotoxin, Reiter's syndrome, gout, acute synovitis, diseases characterized by massive neutrophil infiltration, ankylosing spondylitis, influenze, cerebral malaria, silicosis, bone resorption disease, fever, myalgias due to infection, osteoporosis, multiple myeloma-related bone disorder, neurodegenerative disease caused by traumatic injury, and traumatic brain injury.

The inventive compounds may also be used to treat acute or chronic graft vs host reactions (e.g., pancreatic islet allograft), acute or chronic transplant rejection (e.g., kidney, liver, heart, lung, pancreas, bone marrow, cornea, small bowel, skin allografts, skin homografts, heterografts, and/or cells derived from such organs), and skin conditions including, but not limited to scar tissue formation, eczema, atopic dermatitis, contact dermatitis, urticaria, schleroderma, scleraclerma, and psoriasis. The inventive compounds also may be used to treat allergies and respiratory conditions, including asthma, acute respiratory distress syndrome, hayfever, allergic rhinitis, and any chronic pulmonary inflammatory disease such as chronic obstructive pulmonary disease. The compounds further may be used to treat steroid resistance in asthma and allergies.

Additionally, the inventive compounds may be used to treat inflammation associated with autoimmune diseases including, but not limited to, systemic lupus erythematosis, Addison's disease, autoimmune polyglandular disease (also known as autoimmune polyglandular syndrome), and Grave's disease. The inventive compounds may be used to infectious diseases such as sepsis, septic shock, Shigellosis, and Heliobacter Pylori.

The compounds may be used to treat viral diseases including herpes simplex type 1 (HSV-1), herpes simplex type 2 (HSV-2), cytomegalovirus, Epstein-Barr, human immunodeficiency virus (HIV), acute hepatitis infection (including hepatitis A, hepatits B, and hepatitis C), HIV infection and CMV retinitis, AIDS, ARC or malignancy, and herpes.

The inventive compounds also may be used to treat angiogenic disorders including solid tumors, ocular neovasculization, and infantile haemangiomas.

In addition, p38 inhibitors of this invention inhibit the expression of inducible pro-inflammatory proteins such as prostaglandin endoperoxide synthase-2 (PGHS-2), also referred to as cyclooxygenase-2 (COX-2). Accordingly, additional conditions that may be treated with the inventive compounds include edema, analgesia and pain, such as neuromuscular pain, headache, pain caused by cancer or surgery, dental pain and arthritis pain. In view of their COX-2 inhibitory activity, the inventive compounds also may be used to treat cancer including without limitation epithelial cancer and adenocarcinoma.

Additionally, the compounds of this invention are useful to treat ischemia, including ischemia resulting from vascular occlusion, cerebral infarction, stroke, and related cerebral vascular diseases (including cerebrovascular accident and transient ischemic attack). Accordingly, the compounds may be used to treat myocardial infarction, coronary artery disease, non-Q wave MI, congestive heart failure, ventricular hypertrophy, cardiac arrhythmias, unstable angina, chronic stable angina, Prinzmetal's angina, high blood pressure, intermittent claudication, silent ischemia, cardiac hypertrophy, and peripheral occlusive arterial disease (e.g., peripheral arterial disease, critical leg ischemia, prevention of amputation, and prevention of cardiovascular morbidity such as MI, stroke or death).

Additionally, in view of their activity in treating ischemia, the compounds of the invention may be useful to treat symptoms or consequences occurring from thrombosis, atherosclerosis, peripheral arterial disease, and thrombotic or thromboembolic symptoms or consequences associated with and/or caused by one or more of the following: thromboembolic stroke (including that resulting from atrial fibrillation or from ventricular or aortic mural thrombus), venous thrombosis (including deep vein thrombosis), arterial thrombosis, cerebral thrombosis, pulmonary embolism, cerebral embolism, thrombophilia (e.g., Factor V Leiden, and homocystinenimia), coagulation syndromes and coagulopathies (e.g., disseminated intravascular coagulation), restenosis (e.g., following arterial injury induced endogenously or exogenously), atrial fibrillation, and ventricular enlargement (including dilated cardiac myopathy and heart failure). The compounds of the invention also may be used to treat symptoms or consequences of atherosclerotic diseases and disorders, such as atherosclerotic vascular disease, atherosclerotic plaque rupture, atherosclerotic plaque formation, transplant atherosclerosis, and vascular remodeling atherosclerosis. The compounds of the invention further may be used to treat symptoms or consequences of thrombotic or thromboembolic conditions associated with cancer, surgery, inflammation, systematic infection, artificial surfaces (such as stents, blood oxygenators, shunts, vascular-access ports, vascular grafts, artificial valves, etc.), interventional cardiology such as percutaneous transluminal coronary angioplasty (PTCA), immobility, medication (such as oral contraceptives, hormome replacement therapy, and heparin), pregnancy and fetal loss, and diabetic complications including retinopathy, nephropathy, and neuropathy.

The compounds of the present invention may be used for the preservation of tissue, for example, the preservation of tissue as relates to organ transplantation and surgical manipulation. The compounds may be used to treat diseases or disorders in other tissues or muscles that are associated with ischemic conditions and/or to enhance the strength or stability of tissue and muscles. For example, the compounds may be used to treat muscle cell damage and necrosis and/or to enhance athletes' performance.

Additional diseases and disorders that may be treated with the inventive compounds include irritable bowel syndrome, leukemia, CNS disorders associated with cerebral ischemia, such as cerebral infarction, cerebral edema and the like, and diseases associated with proliferation of smooth muscle cells, mesangial cells, and fibroblasts. Such diseases include renal fibrosis, hepatic fibrosis, prostate hypertrophy, and pulmonary fibrosis.

The inventive compounds also may be used to treat veterinary viral infections, such as lentivirus infections, including, but not limited to, equine infectious anemia virus; or retro virus infections, including feline immunodeficiency virus, bovine immunodeficiency virus, and canine immunodeficiency virus.

When the terms "p38 associated condition" or "p38 associated disease or disorder" are used herein, each is intended to encompass all of the conditions identified above as if repeated at length, as well as any other condition that is modulated by p38 kinase activity.

The present invention thus provides methods for treating such conditions, comprising administering to a subject in need thereof an effective amount of at least one compound of Formula (I), or a pharmaceutically-acceptable salt, hydrate, or prodrug thereof. The methods of treating p38 kinase-associated conditions may comprise administering compounds of Formula (I) alone or in combination with each other and/or other suitable therapeutic agents such as anti-inflammatory drugs, antibiotics, anti-viral agents, antioxidants, cholesterol/lipid lowering agents, anti-tumor agents including antiproliferative agents, and agents used to treat ischemia.

Examples of suitable other anti-inflammatory agents with which the inventive compounds may be used include aspirin, cromolyn, nedocromil, theophylline, zileuton, zafirlukast, monteleukast, pranleukast, indomethacin, and lipoxygenase inhibitors; non-steroidal antiinflammatory drugs (NSAIDs) (such as ibuprofen and naproxin); TNF-α inhibitors (such as tenidap and rapamycin or derivatives thereof), or TNF-α antagonists (e.g., infliximab, enbrel, D2E7, OR1384), cytokine modulators (e.g. TNF-alpha converting enzyme [TACE] inhibitors, Interleukin-1 converting enzyme (ICE) inhibitors, Interleukin-1 receptor antagonists), prednisone, dexamethasone, Enbrel®, cyclooxygenase inhibitors (i.e., COX-1 and/or COX-2 inhibitors such as Naproxen®, Celebrex®, or Vioxx®), CTLA4-Ig agonists/antagonists (LEA29Y), CD40 ligand antagonists, IMPDH inhibitors (such as mycophenolate [CellCept®] and VX-497), integrin antagonists, alpha-4 beta-7 integrin antagonists, cell adhesion inhibitors, interferon gamma antagonists, ICAM-1, prostaglandin synthesis inhibitors, budesonide, clofazimine, CNI-1493, CD4 antagonists (e.g., priliximab), other p38 mitogen-activated protein kinase inhibitors, protein tyrosine kinase (PTK) inhibitors, IKK inhibitors, therapies for the treatment of irritable bowel syndrome (e.g., Zelmac®, Zelnorm®, and Maxi-K® openers such as those disclosed in U.S. Pat. No. 6,184,231 B1), or other NF-κB inhibitors (such calphostin, CSAIDs, and quinoxalines as disclosed in U.S. Pat. No. 4,200,750); corticosteroids (such as beclomethasone, triamcinolone, budesonide, fluticasone, flunisolide, dexamethasone, prednisone, and dexamethasone); disassociated steroids; chemokine receptor modulators (including CCR1, CCR2, CCR3, CCR4, and CXCR2 receptor antagonists); secretory and cytosolic phospholipase A2 inhibitors, VLA4 antagonists, glucocorticoids, salicylates, nitric oxide, and other immunosuppressants; and nuclear translocation inhibitors, such as deoxyspergualin (DSG).

To treat pain, the inventive compounds may be used in combination with aspirin, NSAIDs, or with 5-HT 1 receptor agonists such as buspirone, sumitriptan, eletriptan or rizatriptan.

Examples of suitable antibiotics with which the inventive compounds may be used include β-lactams (e.g., penicillins, cephalosporins and carbopenams); β-lactam and lactamase inhibitors (e.g., augamentin); aminoglycosides (e.g., tobramycin and streptomycin); macrolides (e.g., erythromycin and azithromycin); quinolones (e.g., cipro and tequin); peptides and deptopeptides (e.g vancomycin, synercid and daptomycin) metabolite-based anti-biotics (e.g., sulfonamides and trimethoprim); polyring systems (e.g., tetracyclins and rifampins); protein synthesis inhibitors (e.g., zyvox, chlorophenicol, clindamycin, etc.); and nitro-class antibiotics (e.g., nitrofurans and nitroimidazoles).

Examples of suitable antiviral agents for use with the inventive compounds include nucleoside-based inhibitors, protease-based inhibitors, and viral-assembly inhibitors.

Examples of suitable anti-osteoporosis agents for use in combination with the compounds of the present invention include alendronate, risedronate, PTH, PTH fragment, raloxifene, calcitonin, RANK ligand antagonists, calcium sensing receptor antagonists, TRAP inhibitors, selective estrogen receptor modulators (SERM) and AP-1 inhibitors.

Examples of suitable anti-oxidants for use in combination with the compounds of the present invention include lipid peroxidation inhibitors such as probucol, BO-653, Vitamin A, Vitamin E, AGI-1067, and α-lipoic acid.

A further use of the compounds of this invention is in combination with steriodal or non-steroidal progesterone receptor agonists ("PRA"), such as levonorgestrel, medroxyprogesterone acetate (MPA).

The inventive compounds also may be used in combination with anti-diabetic agents, such as biguanides (e.g. metformin), glucosidase inhibitors (e.g. acarbose), insulins (including insulin secretagogues or insulin sensitizers), meglitinides (e.g. repaglinide), sulfonylureas (e.g., glimepiride, glyburide and glipizide), biguanide/glyburide combinations (e.g., glucovance), thiozolidinediones (e.g. troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in U.S. Ser. No. 09/519,079 filed Mar. 6, 2000 and assigned to the present assignee, glucagon-like peptide-1 (GLP-1), glucagon phosphorylase, and dipeptidyl peptidase IV (DP4) inhibitors.

In addition, the compounds may be used with agents that increase the levels of cAMP or cGMP in cells for a therapeutic benefit. For example, the compounds of the invention may have advantageous effects when used in combination with phosphodiesterase inhibitors, including PDE1 inhibitors (such as those described in Journal of Medicinal Chemistry, Vol. 40, pp. 2196-2210 [1997]), PDE2 inhibitors, PDE3 inhibitors (such as revizinone, pimobendan, or olprinone), PDE4 inhibitors (such as rolipram, cilomilast, or piclamilast), PDE7 inhibitors, or other PDE inhibitors such as dipyridamole, cilostazol, sildenafil, denbutyline, theophylline (1,2-dimethylxanthine), ARIFLO™ (i.e., cis-4-cyano-4-[3-(cyclopentyloxy)-4-methoxyphenyl]cyclohexane-1-carboxylic acid), arofyline, roflumilast, C-11294A, CDC-801, BAY-19-8004, cipamfylline, SCH351591, YM-976, PD-1 89659, mesiopram, pumafentrine, CDC-998, IC-485, and KW-4490.

The inventive compounds may also be useful in combination with anticancer strategies and chemotherapies such as taxol and/or cisplatin. The compounds may be used in conjunction with antitumor agents such as paclitaxel, adriamycin, epithilones, cisplatin, and carboplatin.

In view of their usefulness in treating ischemia, the inventive compounds may be used in combination with agents for inhibiting $F_1F_0$-ATPase, including efrapeptin, oligomycin, autovertin B, azide, and compounds described in U.S. patent application Ser. No. 10/315,818, filed Dec. 10, 2001 and assigned to the present assignee; -alpha- or beta-adrenergic blockers (such as propranolol, nadolol, carvedilol, and prazosin), or -β-adrenergic agonists (such as albuterol, terbutaline, formoterol, salmeterol, bitolterol, pilbuterol, and fenoterol); antianginal agents such as nitrates, for example, sodium nitrates, nitroglycerin, isosorbide mononitrate, isosorbide dinitrate, and nitrovasodilators; antiarrhythmic agents including Class I agents (such as propafenone); Class II agents (propranolol); Class III agents (such as sotalol, dofetilide, amiodarone, azimilide and ibutilide); Class IV agents (such as diltiazem and verapamil); $K^+$ channel modulators such as $I_{Ach}$ inhibitors and inhibitors of the $K_v1$ subfamily of $K^+$ channel openers such as $I_{Kur}$ inhibitors (e.g., compounds disclosed in U.S. application Ser. No. 09/729,731, filed Dec. 5, 2000); and gap-junction modulators such as connexions; anticoagulant or antithrombotic agents including aspirin, warfarin, ximelagtran, low molecular weight heparins (such as lovenox, enoxaparain, and dalteparin), anti-platelet agents such as GPIIb/GPIIIa blockers, (e.g., abciximab, eptifibatide, and tirofiban), thromboxane receptor antagonists (e.g., ifetroban), $P2Y_1$ and $P2Y_{12}$ antagonists (e.g., clopidogrel, ticlopidine, CS-747, and aspirin/clopidogrel combinations), and Factor Xa inhibitors (e.g., fondaprinux); and diuretics such as sodium-hydrogen exchange inhibitors, chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, and amiloride.

Additionally, the inventive compounds may be used in combination with lipid profile modulators and antiatherosclerotic agents including HMG-CoA reductase inhibitors (e.g., pravastatin, simvastatin, atorvastatin, fluvastatin, cerivastatin, AZ4522, itavastatin [Nissan/Kowa]), ZD-4522 (a.k.a. rosuvastatin, atavastatin or visastatin), pravachol, squalene synthetase inhibitors, fibrates, bile acid sequestrants (such as questran), niacin and niacin/statin combinations, lipooxygenase inhibitors, ileal $Na^+$/bile acid cotransporter inhibitors, ACAT 1 inhibitors, ACAT2 inhibitors, dual ACAT1/2 inhibitors, microsomal triglyceride transport protein inhibitors (such as disclosed in U.S. Pat. Nos. 5,739,135, 5,712,279 and 5,760,246), cholesterol absorption inhibitors (such as Zetia®), cholesterol ester transfer protein inhibitors (e.g., CP-529414), PPAR-delta agonists, PPAR-alpha agonists, dual PPAR-alpha/delta agonists, LXR-alpha agonists, LXR-beta agonists, LXR dual alpha/beta agonists, and SCAP modulators.

The combination of the inventive compounds with other therapeutic agents may prove to have additive and synergistic effects. The combination may be advantageous to increase the efficacy of the administration or decrease the dosage to reduce possible side-effects.

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds.

The present invention also provides pharmaceutical compositions capable of treating p38-kinase associated conditions, including TNF-α, IL-1, and/or IL-8 mediated conditions, as described above. The inventive compositions may contain other therapeutic agents as described above. Pharmaceutical compositions may be formulated by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulations.

The compounds of Formula (I) may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The effective amount of a compound of the present invention may be determined by one of ordinary skill in the art, and includes exemplary dosage amounts for a mammal of from about 0.05 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species, that are affected by mediation of p38 enzyme levels.

Compounds of within the scope of formula (I) may be tested for activity as inhibitors of p38α/β enzymes and TNF-α using the assays described below, or variations thereof that are within the level ordinary skill in the art. Compounds described in the examples herein have shown surprisingly advantageous activity as kinase inhibitors, particularly inhibitors of p38α/β enzymes.

Biological Assays

Generation of p38 Kinases cDNAs of human p38α, β and γ isozymes are cloned by PCR. These cDNAs can be subcloned in the pGEX expression vector (Pharmacia). GST-p38 fusion protein is expressed in *E. Coli* and purified from bacterial pellets by affinity chromatography using glutathione agarose. p38 fusion protein is activated by incubating with constitutively active MKK6. Active p38 is separated from MKK6 by affinity chromatography. Constitutively active MKK6 is generated according to Raingeaud et al. [*Mol. Cell. Biol.*, 1247-1255 (1996)].

TNF-α Production by LPS-Stimulated PBMCs

Heparinized human whole blood is obtained from healthy volunteers. Peripheral blood mononuclear cells (PBMCs) are purified from human whole blood by Ficoll-Hypaque density gradient centrifugation and resuspended at a concentration of $5 \times 10^6$/ml in assay medium (RPMI medium containing 10% fetal bovine serum). 50 ul of cell suspension is incubated with 50 ul of test compound (4× concentration in assay medium containing 0.2% DMSO) in 96-well tissue culture plates for 5 minutes at RT. 100 ul of LPS (200 ng/ml stock) is then added to the cell suspension and the plate is incubated for 6 hours at 37° C. Following incubation, the culture medium is collected and stored at −20° C. TNF-α concentration in the medium is quantified using a standard ELISA kit (Pharmingen-San Diego, Calif.). Concentrations of TNF-α and $IC_{50}$ values for test compounds (concentration of compound that inhibited LPS-stimulated TNF-α production by 50%) are calculated by linear regression analysis.

p38 Assay

The assays are performed in V-bottomed 96-well plates. The final assay volume is 60 μl prepared from three 20 μl additions of enzyme, substrates (MBP and ATP) and test compounds in assay buffer (50 mM Tris pH 7.5, 10 mM $MgCl_2$, 50 mM NaCl and 1 mM DTT). Bacterially expressed, activated p38 is pre-incubated with test compounds for 10 min. prior to initiation of reaction with substrates. The reaction is incubated at 25° C. for 45 min. and terminated by adding 5 μl of 0.5 M EDTA to each sample. The reaction mixture is aspirated onto a pre-wet filtermat using a Skatron Micro96 Cell Harvester (Skatron, Inc.), then washed with PBS. The filtermat is then dried in a microwave oven for 1 min., treated with MeltilLex A scintillation wax (Wallac), and counted on a Microbeta scintillation counter Model 1450 (Wallac). Inhibition data are analyzed by nonlinear least-squares regression using Prizm (GraphPadSoftware). The final concentration of reagents in the assays are ATP, 1 μM; [γ-$^{33}$P]ATP, 3 nM; MBP (Sigma, #M1891), 2 μg/well; p38, 10 nM; and DMSO, 0.3%.

TNF-α Production by LPS-Stimulated Mice

Mice (Balb/c female, 6-8 weeks of age, Harlan Labs; n=8/treatment group) are injected intraperitoneally with 50 ug/kg lipopolysaccharide (LPS; *E coli* strain 0111:B4, Sigma) suspended in sterile saline. Ninety minutes later, mice are sedated by $CO_2$:$O_2$ inhalation and a blood sample was obtained. Serum is separated and analyzed for TNF-alpha concentrations by commercial ELISA assay per the manufacturer's instructions (R&D Systems, Minneapolis, Minn.).

Test compounds are administered orally at various times before LPS injection. The compounds are dosed either as suspensions or as solutions in various vehicles or solubilizing agents.

Abbreviations

For ease of reference, the following abbreviations are employed herein, including the methods of preparation and Examples that follow:

Ph=phenyl
Bz=benzyl
t-Bu=tertiary butyl
Me=methyl
Et=ethyl
Pr=propyl
n-propyl or n-Pr=straight chain propyl
Iso-P, iPr, iso-Pr=isopropyl
MeOH=methanol
EtOH=ethanol
EtOAc=ethyl acetate
Boc=tert-butyloxycarbonyl
BOP=benzotriazol-1-yloxy-tris(dimethylamino)-phosphonium hexafluorophosphate
Bt=benzotriazolyl DCM=dichloromethane
DCE=1,2-dichloroethane
DIPEA=diisopropylethylamine
DMF=N, N-dimethyl formamide
DMF-DMA=N, N-dimethyl formamide dimethyl acetal
DMSO=dimethyl sulfoxide
DPPA=diphenylphosphoryl azide
EDC or EDCI=1-(3-Dimethylaminopropyl)-3-ethylcarbodiimide hydrochloride
HATU=O-(7-Azabenzotriazol-1-yl-N,N,N',N'-tetramethyluronim hexafluorophosphate
HOBt=1-hydroxybenzotriazole hydrate
IPA=isopropanol (isopropyl alcohol)
KOH=potassium hydroxide
$K_2CO_3$=potassium carbonate
LDA=lithium diisopropylamide
$POCl_3$=phosphorous oxychloride
m-CPBA=m-chloroperbenzoic acid
NaH=sodium hydride
NaOH=sodium hydroxide
p-TsOH=p-toluenesulfonic acid
Pd=palladium
Pd/C=palladium on carbon
TFA=trifluoroacetic acid
THF=tetrahydrofuran
min=minute(s)
h or hr=hour(s)
L=liter
mL=milliliter
μL=microliter
g=gram(s)
mg=milligram(s)
mol=moles
mmol=millimole(s)
meq=milliequivalent
RT or rt=room temperature
ret. t.=HPLC retention time (minutes)
sat or sat'd=saturated
aq.=aqueous
TLC=thin layer chromatography
HPLC=high performance liquid chromatography
RP HPLC=reverse phase HPLC
Prep HPLC=preparative reverse phase HPLC
LC/MS=high performance liquid chromatography/mass spectrometry
MS=mass spectrometry
NMR=nuclear magnetic resonance
mp=melting point Methods of Preparation Compounds of Formula (I) may be prepared according to the following Schemes and the knowledge of one skilled in the art. Variables in the schemes (e.g., $R_2$, $R_3$, $R_4$, $R_6$, $R_7$, $R_8$, $Q^*$, etc.) are as defined above for compounds of formula (I). Solvents, temperatures, pressures, and other reaction conditions may readily be selected by one of ordinary skill in the art.

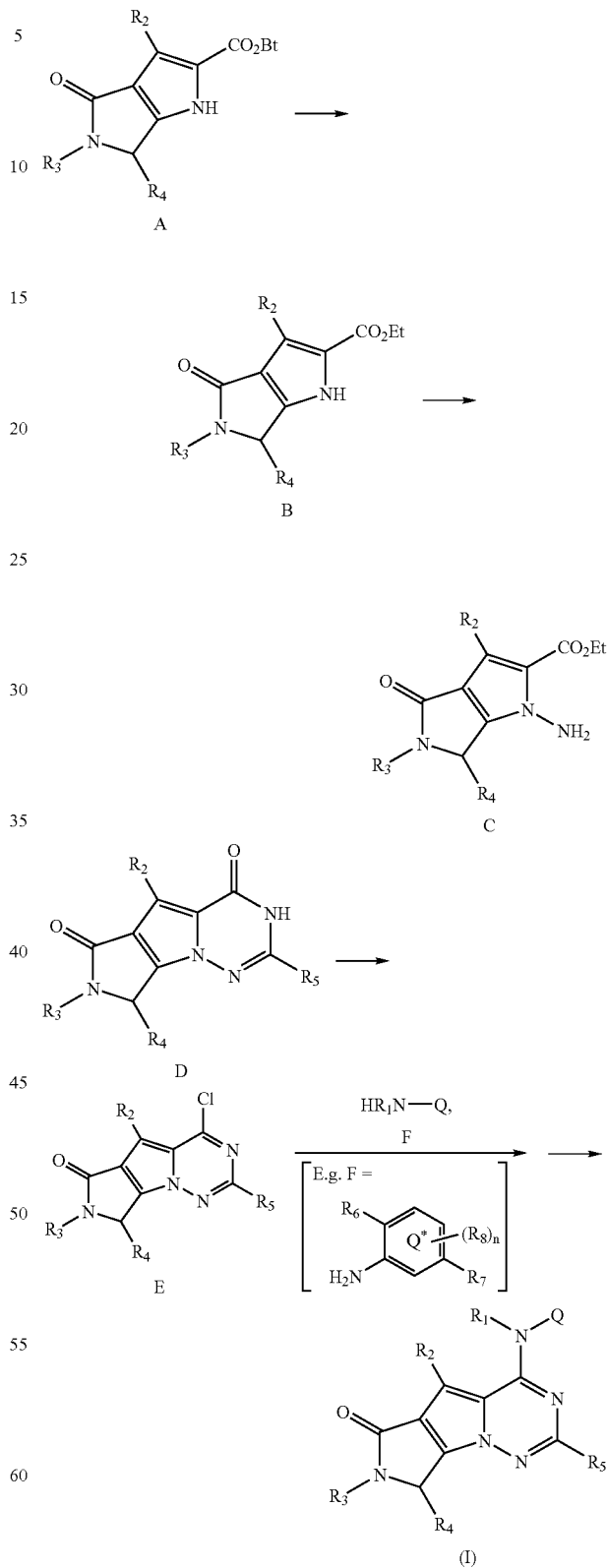

Scheme I

Compounds having the formula (I) can be prepared as shown in Scheme I. Compounds A can be treated with base such as NaOH in solvent such as EtOH to produce compounds B. Compounds B can be aminated via reaction with chloramine NH$_2$Cl, to produce compounds C. Compounds C can be cyclized upon reaction with formamide (R$_5$=H), or other amide R$_5$C(=O)NH$_2$, at elevated temperature to produce compounds D. Compounds D can be chlorinated (or halogenated) upon reaction with halogenating agent such as POCl$_3$ in solvent such as toluene at elevated temperature, to provide compounds E. Compounds E can be coupled with appropriately-substituted phenyl or pyridyl compounds (F) (see also Schemes Ia-Ib) to provide compounds of formula (I). See also U.S. Pat. No. 6,670,357, U.S. publication 2003/0186982A1, published Oct. 2, 2003, U.S. application Ser. No. 10/773,002, filed Feb. 5, 2004, and U.S. application Ser. No. 60/620,784, filed concomitantly herewith, all of which applications are assigned to the present assignee. Additionally, applicant incorporates by reference the examples anad methods of preparation of each of these patents and applications.

Compound F-1 (wherein Q* is phenyl and R$_7$ is —C(=O)NHR$_{10}$) can be prepared as outlined in Scheme 1a by 1) reacting a 3-nitro-benzoyl chloride (1a-1) (which is commercially available or can be prepared by one skilled in the art) and an amine H$_2$N—R$_{10}$ in CH$_2$Cl$_2$ to give a nitro intermediate (1a-2); and 2) reducing (1a-2) under conditions such as hydrogen gas and a catalyst in a solvent to afford aniline F. The salt form can be prepared by reacting F with an appropriate acid (e.g., HCl).

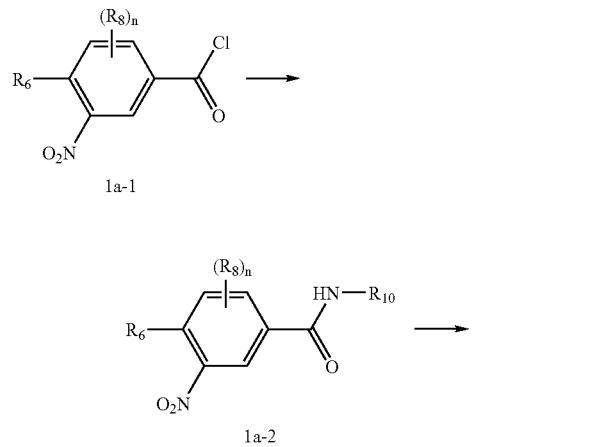

Scheme 1a

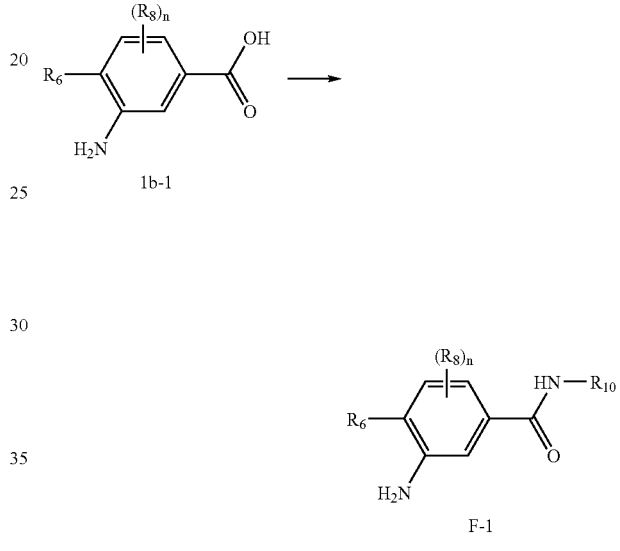

Scheme 1b

Alternatively, compound F-1 (wherein Q* is phenyl and R$_7$ is —C(=O)NHR$_{10}$) can be prepared as outlined in Scheme 1b, by reacting a 3-amino-benzoic acid (1b-1) (which is commercially available or can be prepared by one skilled in the art) with the amine H$_2$N—R$_{10}$ in the presence of a coupling agent, such as EDC/HOBt, in a suitable solvent. The salt form can be prepared by reacting compound F with an appropriate acid (e.g., HCl).

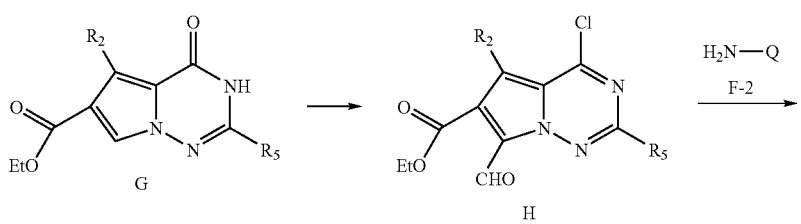

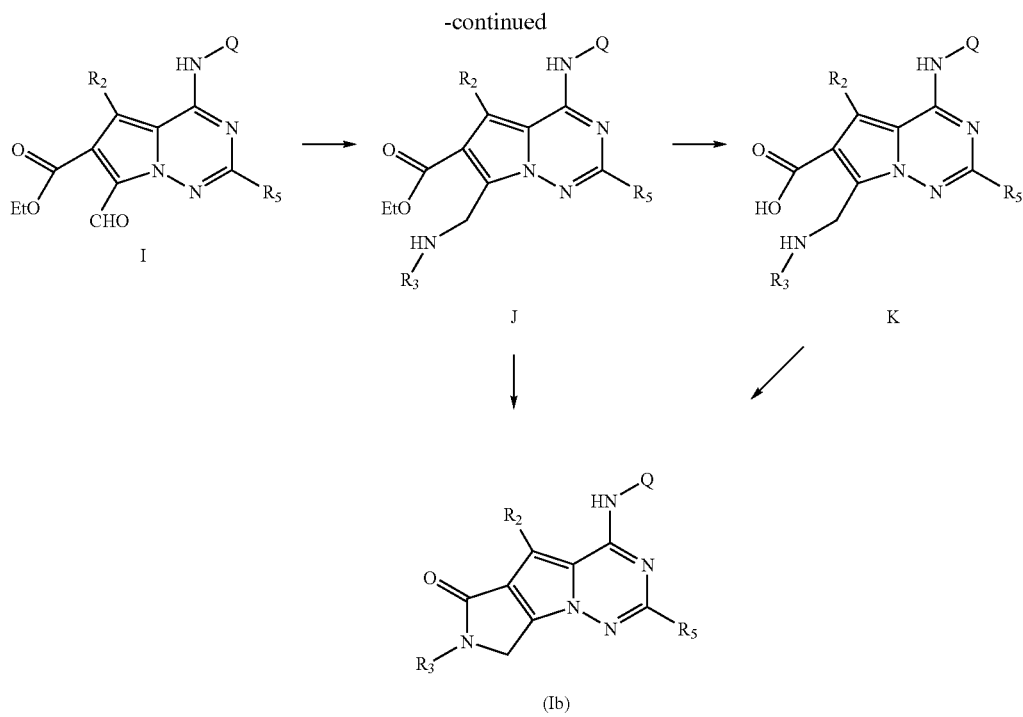

Compounds of formula (Ib) can be prepared as shown in Scheme II. Compounds G can be reacted with a halogenating agent such as POCl₃ in solvent such as DMF to provide aldehyde compounds H. Compounds H can be coupled with appropriately-substituted phenyl or pyridyl compounds (F-2), such as benzamide compounds of Schemes Ia-Ib, to provide compounds I.

Compounds I can be reacted with an appropriate amine NHR₃ in solvent such as THF in the presence of a reducing agent such as sodium triacetoxyborohydride to provide compounds J. Compounds J can be directly converted to compounds of formula (Ib) upon reaction with LDA in solvent or solvent mixture and THF at reduced temperature. Alternatively, compounds J can be first hydrolyzed to acids K upon addition of base such as NaOH in solvent such as MeOH and THF, then converted to compounds of formula (Ib) upon addition of HOBt and EDAC in solvent such as DMF. Compounds G can be prepared as shown in Scheme IIa or alternatively as described in U.S. application Ser. No. 10/773,002, filed Feb. 5, 2004, assigned to the present assignee, the examples and methods of preparation of which are incorporated herein by reference.

Scheme IIa

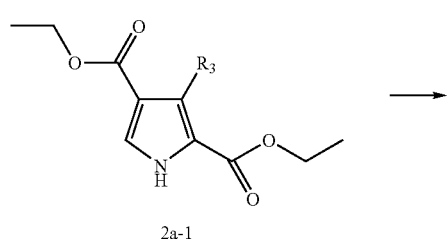

3-methyl-1-pyrrole-2,4-diethyl ester (2a-1) can be reacted with chloramine in ether to produce compound (2a-2). Reacting compound (2a-2) in formamide ($R_5$=H), or other amide $R_5C(=O)NH_2$, with acetic acid produces compounds G. Compounds G wherein $R_5$ is other than hydrogen also can be prepared as described in U.S. application Ser. No. 10/773, 002, filed Feb. 5, 2004, assigned to the present assignee, the examples and methods of preparation of which are incorporated herein by reference.

In addition, other compounds of formula (I) may be prepared using procedures generally known to those skilled in the art. In particular, the following examples provide additional methods for the preparation of the compounds of this invention.

In the following exemplary embodiments of the invention, HPLC purifications were done on C18 reverse phase (RP) columns using water MeOH mixtures and TFA as buffer solution. These examples are illustrative rather than

EXAMPLES

Example 1

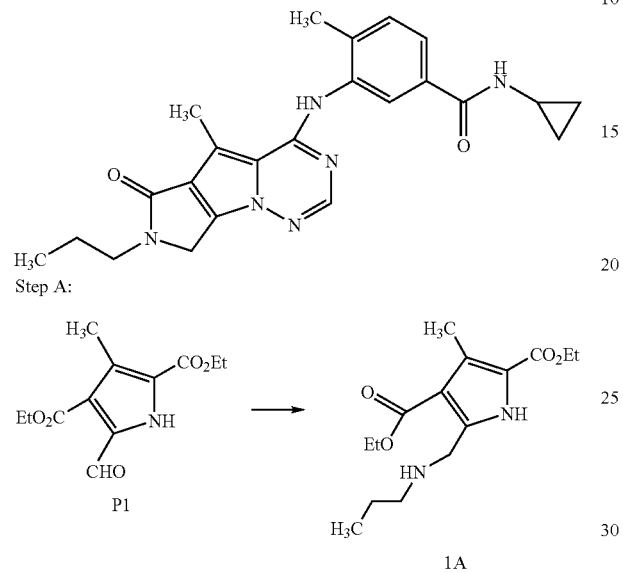

Step A:

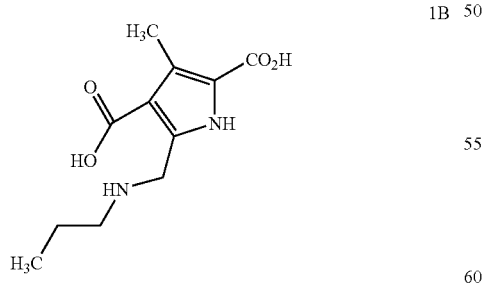

To a solution of P1 (3.17 g, 12.5 mmol, 1.0 eq.) and n-propylamine (1.1 mL, 13.4 mmol, 1.1 eq.) in THF (50 mL) under nitrogen was added NaBH(OAc)$_3$ (4.07 g, 19.2 mmol, 1.5 eq.). After stirring overnight, the reaction mixture was concentrated in vacuo, and the residue was diluted with CH$_2$Cl$_2$ and water. After separation of the layers, the aqueous layer was extracted with CH$_2$Cl$_2$, and the organic layers were combined, washed with saturated aqueous NaHCO$_3$, dried over Na$_2$SO$_4$, filtered and concentrated in vacuo. Silica gel chromatography using CH$_2$Cl$_2$:MeOH (20:1) as eluent afforded compound 1A as a light yellow solid (2.43 g, 66%). HPLC RT=2.393 min (100%, 220 nm); LC/MS (MH)=297.00.

Step B:

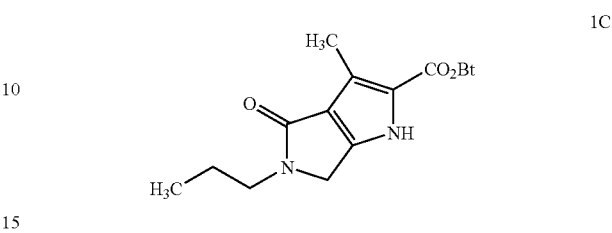

A solution of compound 1A (R=n-Pr; 2.43 g, 8.2 mmol, 1.0 eq.), THF (16 mL) and aqueous NaOH (1 N, 35 mL, 35 mmol, 4.3 eq.) was refluxed overnight. After cooling to room temperature, the reaction mixture was concentrated in vacuo not to dryness. At 0° C., aqueous HCl (6 N) was added until pH~5 by litmus paper. The precipitate was collected, washed with water and dried to give compound 1B as a white solid (1.78 g, 90% yield). HPLC RT=1.023 min (96%, 220 nm); LC/MS (MH)=241.12.

Step C:

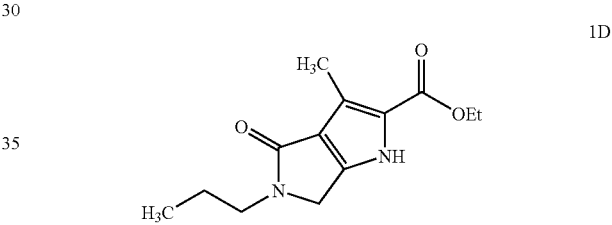

A solution of compound 1B (0.91 g, 3.8 mmol, 1.0 eq.), EDAC (1.6 g, 8.4 mmol, 2.2 eq.), HOBt (1.1 g, 8.4 mmol, 2.2 eq.) and DMF (200 mL) was heated under nitrogen at 55° C. After 0.5 h, the reaction mixture was cooled to room temperature, and the solvent was removed by distillation. The residue was dissolved in CH$_2$Cl$_2$, washed successively with water and aqueous sat'd NaHCO$_3$, dried over Na$_2$SO$_4$, filtered and concentrated in vacuo. Trituration with Et$_2$O afforded crude compound 1C as a tan solid which was used without further purification. HPLC RT=2.850 min (84%, 220 nm); LC/MS (MH)=350.15.

Step D:

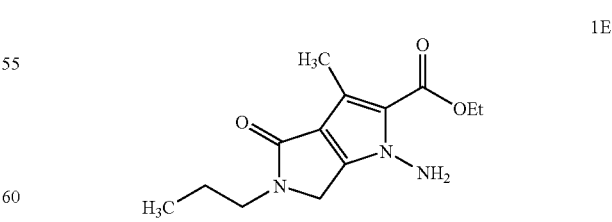

A solution of compound 1C (0.425 g, 1.25 mmol, 1.00 eq.) in sodium ethoxide (21% solution in EtOH, 5.0 mL) was stirred for 30 min. and then concentrated in vacuo. The residue was diluted with DCM and water, and the layers were separated. The organic layer was washed with saturated aqueous sodium bicarbonate and brine, dried over sodium sulfate, filtered, and concentrated in vacuo. Trituration with diethyl ether provided crude 1D as a tan solid (0.342 g) which was used without purification. HPLC: RT=2.613 min. (100%, 220 nm); LC/MS (MH)$^+$=251.11.

Step E:

To a solution of sodium hydride (95% in mineral oil, 0.0684 g, 2.71 mmol, 2.17 eq.) in DMF (5.0 mL) under nitrogen at 0° C. was added compound 1D (assumed 1.25 mmol, 1.00 eq.). The ice bath was removed, and the reaction was stirred to room temperature for 30 min. Chloramine (0.15 M in diethyl ether, 20 mL, 3.00 mmol, 2.40 eq.) was then added. After 1 hr, the reaction was cooled to 0° C. Aqueous Na$_2$S$_2$O$_3$ (1 M, 11 mL) and water (20 mL) were added. The ice bath was removed, and the reaction was stirred to room temperature for 30 min. The solution was extracted with EtOAc twice, and the organic layers were combined, washed with brine, dried over sodium sulfate, filtered, and concentrated in vacuo. Silica gel chromatography (DCM:MeOH, 100:1) afforded compound 1E (0.237 g, 71.6% yield). HPLC: RT=2.593 min. (<100%, 220 rm); LC/MS (MH)$^+$=266.04.

Step F:

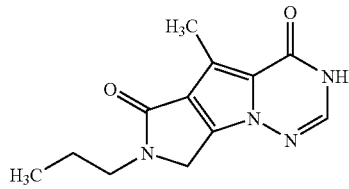

1F

A solution of compound 1E (0.235 g, 0.895 mmol, 1.00 eq.) in formamide (9.0 mL) was heated under nitrogen at 180° C. After 3 hr, the hot bath was removed, and the solution was cooled to room temperature. At 0° C., ice was added, and the solution was stirred for 1 h. DCM was added, and the layers were separated. The aqueous layer was extracted by DCM (5×), and the organic layers were combined, dried over sodium sulfate, filtered, and concentrated in vacuo. Silica gel chromatography (DCM:MeOH, 20:1) afforded compound 1F (0.158 g, 72.0% yield). HPLC: RT=2.210 min. (<100%, 220 nm); LC/MS (MH)$^+$=247.07.

Step G:

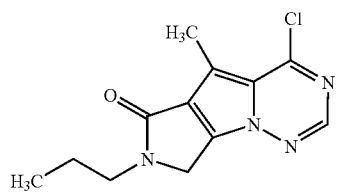

1G

A solution of compound 1F (0.0947 g, 0.384 mmol, 1.00 eq.), phosphorus oxychloride (0.075 mL, 0.805 mmol, 2.09 eq.), disopropylethyl amine (0.080 mL, 0.460 mmol, 1.20 eq.) in toluene (1.0 mL) was heated under nitrogen at 70° C. for 18 hr. After cooling to room temperature, the solution was concentrated in vacuo to give crude compound 1G which was used immediately in the next step.

Step H:

A solution of compound 1G (assumed 0.384 mmol, 1.00 eq.) and 3-Amino-N-cyclopropyl-4-methyl-benzamide hydrochloride (0.0900 g, 0.473 mmol, 1.23 eq.) in DMF (1.0 mL) was stirred under nitrogen at room temperature overnight. It was then diluted with MeOH and subjected to autopreparative HPLC. The appropriate fractions were collected and basified by addition of solid sodium bicarbonate. The solution was concentrated in vacuo not to dryness, and the aqueous layer was extracted with DCM (2×). The organic layers was combined, dried over sodium sulfate, filtered and concentrated in vacuo. Trituration with diethyl ether provided Example 1 as a brown solid (0.0101 g, 6.3% for two steps). HPLC: RT=2.853 min. (>93%, 220 nm); LC/MS (MH)$^+$=419.09. 3-Amino-N-cyclopropyl-4-methyl-benzamide hydrochloride can be prepared from commercially-available 3-amino-4-methylbenzoic acid as described in Schemes 1a-1b, above, and in WO 03/090912 and U.S. Pat. No. 6,670,357, incorporated herein by reference.

Example 2

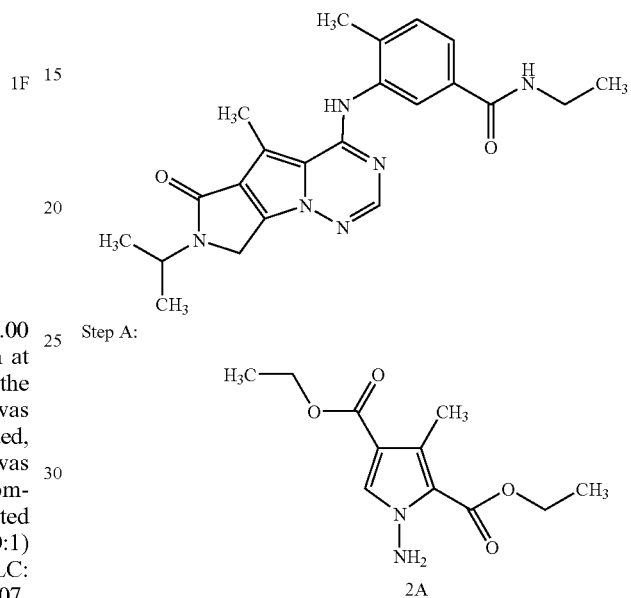

Step A:

2A

To a solution of the 3-methyl-1-pyrrole-2,4-diethyl ester (100 mg) (*J. Heterocyclic Chem.*, Vol. 34 (1997), at pp. 177-193; *Heterocycles*, Vol. 50 (1999), at pp. 853-866; *Synthesis* (1999), at pp. 479-482), in DMF (0.44M) was added either NaH or KOtBu (1.2 equiv) at rt. This solution was stirred for 30-45 minutes. Chloramine in ether (ca. 0.15M, 1 eq.) was added via syringe. The solution was stirred for 1.5 h or until starting material was converted to product as judged by HPLC analysis. The reaction was then quenched with aq. Na$_3$S$_2$O$_3$ and extracted with EtOAc or Et$_2$O. The organic extracts were washed with water and brine and then dried over sodium sulfate. Compound 2A was obtained in >90% yield. NH$_2$Cl in ether was prepared according to the procedure of Nunn, *J. Chem. Soc.* (C), (1971) at p. 823.

Step B:

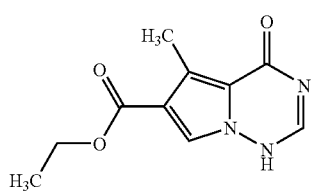

2B

To a solution of Compound 2A (2 g) in formamide (8 mL) was added acetic acid (20% by weight), and the mixture was heated at 120° C. for 24 h. The reaction mixture was cooled, and water was added (32 mL) to precipitate the product. The solids were collected by filtration and washed with EtOAc to furnish Compound 2B as a yellow solid (90%).

Step C:

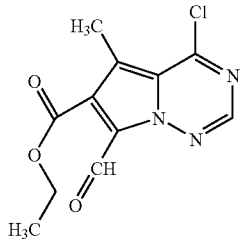

2C

A solution of compound 2B (25.05 g, 113 mmol, 1.00 eq.) in phosphorus oxychloride (75 mL) and DMF (18 mL) was heated at 95° C. under nitrogen for 16 h. After cooling to room temperature, the reaction mixture was added to saturated aqueous sodium bicarbonate (3000 mL) at 4° C. over 1 h 20 min; the inner temperature was kept below 8° C. After the addition was completed, the solution was stirred for 30 min. The cold bath was then removed, and the solution was stirred to room temperature for two hours. The precipitate was filtered, washed with water (1000 mL) and DCM (1500 mL). The organic layer was collected, dried over sodium sulfate, filtered and concentrated in vacuo to give crude compound 2C as a yellow solid (15.85 g, 52.3%) which was used without purification in the next step.

Step D:

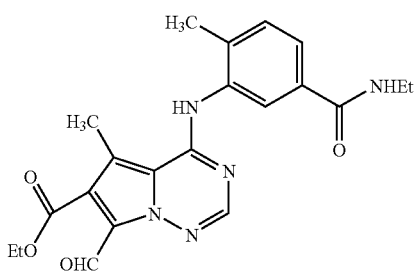

2D

A solution of compound 2C (15.85 g, 59.2 mmol, 1.00 eq.) and 3-Amino-N-ethyl-4-methyl-benzamide hydrochloride (13.19 g, 74.0 mmol, 1.25 eq.) (see Step 1H, above) in DMF (100 mL) was heated at 55° C. under nitrogen for 24 h. DMF was removed under vacuum by short-path distillation at 55° C. The residue was diluted with EtOAc and washed with saturated aqueous sodium bicarbonate (2×) and 10% aqueous lithium chloride. The organic layer was dried over sodium sulfate, filtered and concentrated in vacuo to give crude 2D as a yellow solid (25.81 g) which was used without purification. HPLC: RT=2.733 min.; LC/MS (MH)$^+$= 410.30.

Step E:

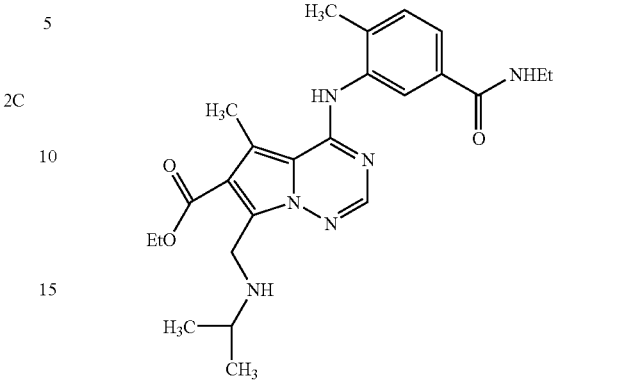

2E

To a solution of compound 2D (assumed 59.2 mmol, 1.00 eq.) and isopropyl amine (10.1 mL, 118.6 mmol. 2.00 eq.) in THF (240 mL) at 0° C. under nitrogen was added sodium triacetoxyborohydride (25.93 g, 122.3 mmol, 2.07 eq.). After 30 min., the cold bath was removed, and the reaction mixture was stirred to room temperature for 2 h. It was then concentrated in vacuo, diluted with EtOAc and saturated aqueous sodium bicarbonate. After separation, the aqueous layer was extracted with EtOAc, and the organic layers were combined, dried over sodium sulfate, filtered and concentrated in vacuo. Trituration with diethyl ether:MeOH (9:1) and DCM afforded compound 2E as an off-white solid (11.79 g, 44.0% for 2 steps). HPLC: RT=2.270 min. (100%, 220 nm); LC/MS(MH)$^+$=453.33.

Step F:

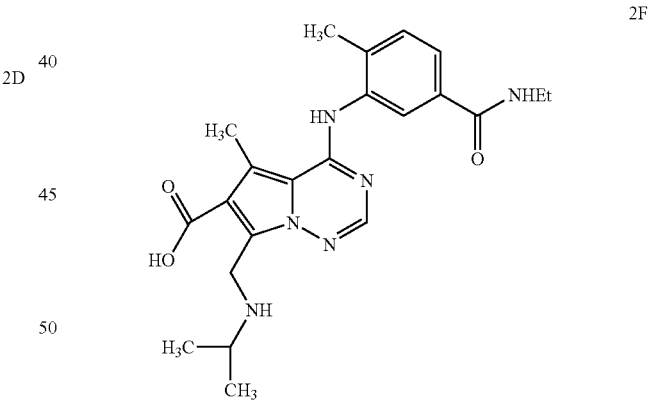

2F

A solution of compound 2E (11.35 g, 25.1 mmol, 1.00 eq.) in THF (15 mL), MeOH (35 mL) and aqueous NaOH (1N, 100 mL, 100 mmol, 3.98 eq.) was refluxed for 9.5 h. After cooling to room temperature, the solution was concentrated in vacuo not to dryness. At 0° C., aqueous HCl (6N) was added until pH ~5-6 by litmus paper. The precipitate was filtered, washed with water, diethyl ether and dried to give compound 2F as a white solid (8.87 g, 83%). HPLC: RT=1.827 min. (93%, 220 nm); LC/MS (MH)$^+$=425.43.

Step G:

A solution of compound 2F (4.00 g, 9.42 mmol, 1.00 eq.), HOBt (1.53 g, 11.3 mmol, 1.20 eq.) and EDAC (2.20 g, 11.5 mmol, 1.22 eq.) in DMF (32 mL) was heated at 55° C. under nitrogen for 2.5 h. After cooling to room temperature, water (200 mL) was added, and the precipitate was filtered, washed with water and diethyl ether. The precipitate was then triturated with EtOAc and ethanol, dried to give Example 2 as a white solid (2.29 g, 60% yield). HPLC: RT=2.420 min. (100%, 220 nm); LC/MS (MH)$^+$=407.33.

Alternate Method of Making Example 2 from Compound 2E

Alternatively to Steps 2F and 2G, Example 2 was made directly from compound 2E, by adding LDA (2.0 M in heptane/THF/ethylbenzene, 1.66 mL, 3.31 mmol) to a solution of compound 2E (0.250 g, 0.552 mmol) in dry THF (10 mL), at −10° C. over 10 min. The resulting mixture was stirred for 6 h, during which period the cold bath temperature was allowed to rise from −10° C. to 10° C. The reaction was quenched with glacial acetic acid (1 mL). The mixture was then diluted with EtOAc (75 mL), washed with 1 N NaOH solution (2×10 mL) and brine, and dried over anhydrous MgSO$_4$. Evaporation of solvent under vacuum and trituration of the residue with diethyl ether provided Example 2 as a white solid 0.123 g, 55% yield).

Examples 3 to 19

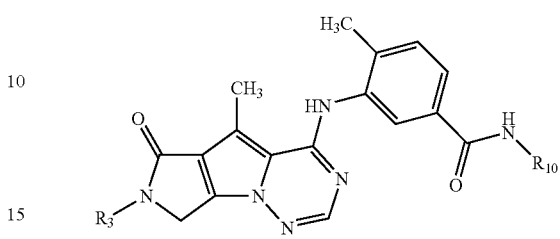

Compounds having the formula immediately above, wherein R$_3$ and R$_{10}$ have the values reported in Table 1, were prepared following the same or similar methods of Examples 1 and 2, using the appropriate amine and benzamide compounds.

TABLE 1

| Ex. No. | R$_3$ | R$_{10}$ | HPLC ret. time (min) | (M + H)$^+$ |
|---|---|---|---|---|
| 3 | | | 2.28 | 391.2 |
| 4 | | | 3.79 | 497.2 |
| 5 | | | 2.85 | 419.2 |
| 6 | | | 2.59 | 405.2 |
| 7 | | | 1.96 | 468.3 |
| 8 | | | 2.44 | 435.3 |
| 9 | | | 2.77 | 419.1 |

TABLE 1-continued
| Ex. No. | R₃ | R₁₀ | HPLC ret. time (min) | (M + H)⁺ |
|---|---|---|---|---|
| 10 |  | 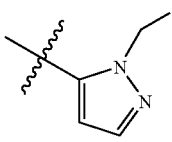 | 2.46 | 459.3 |
| 11 | 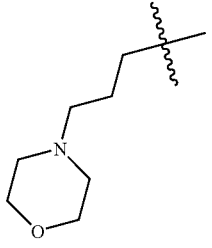 | 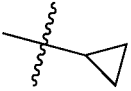 | 1.79 | 504.2 |
| 12 | 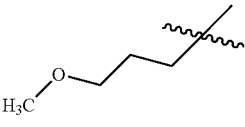 |  | 2.60 | 449.1 |
| 13 | 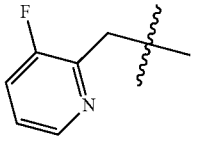 | 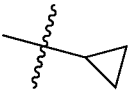 | 2.71 | 486.1 |
| 14 | 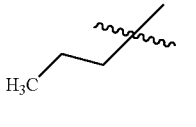 | 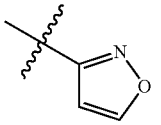 | 2.79 | 446.0 |
| 15 | 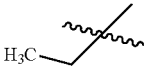 | 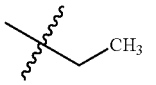 | 2.51 | 393.1 |
| 16 | 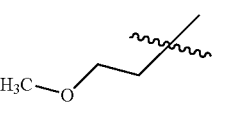 | 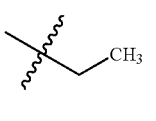 | 2.47 | 423.2 |
| 17 |  | 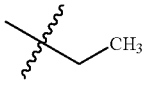 | 2.27 | 379.2 |
| 18 | 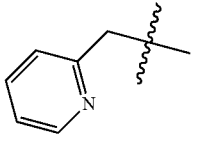 | 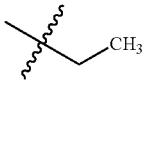 | 1.96 | 456.2 |
| 19 | 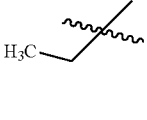 | 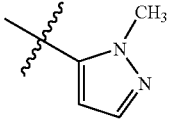 | 2.60 | 445.2 |

Example 20

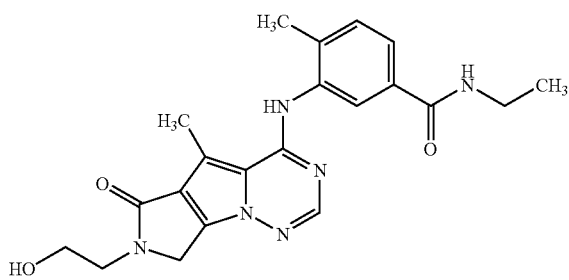

To a solution of Example 16 (0.220 g, 0.521 mmol) in 1,2-dichloroethane (30 mL) was added BBr$_3$ (0.25 mL, 2.64 mmol) at 0° C. over 5 min. The mixture was stirred at 0° C. for 3 h before it was poured into a mixture of water (100 mL) and THF (30 mL). The resulting mixture was stirred at rt overnight, and then basified with concentrated ammonium hydroxide to pH 12. The organic layer was separated, and the aqueous was extracted with EtOAc (3 times). The combined extract was dried over anhydrous MgSO$_4$. After solvent was removed under vacuum, the residue was purified by chromatography (10% MeOH/DCM) to give Example 22 (98 mg, 46% yield) as a white solid. HPLC retention time: 1.92 min; (M+H)$^+$=409.33.

The invention claimed is:
1. A compound having the formula (I),

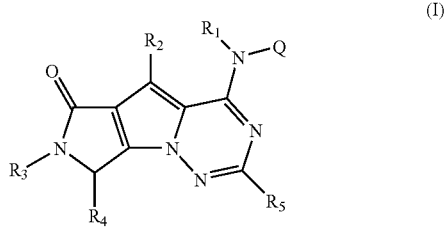

(I)

wherein:
Q is aryl or heteroaryl, wherein said aryl or heteroaryl is optionally substituted with 0 to 2 R$_6$, 0 to 2 R$_7$, and 0 to 1 R$_8$;
R$_1$ is hydrogen or C$_{1-4}$alkyl;
R$_2$ and R$_4$ are independently selected from hydrogen, alkyl, substituted alkyl, alkenyl, substituted alkenyl, halogen, cyano, nitro, amino, alkylamino, hydroxy, alkoxy, substituted alkoxy, cycloalkyl, substituted cycloalkyl, aryl, substituted aryl, heterocyclo, substituted heterocyclo, heteroaryl, and substituted heteroaryl;
R$_3$ and R$_5$ are selected from hydrogen, alkyl, substituted alkyl, alkenyl, substituted alkenyl, cycloalkyl, substituted cycloalkyl, aryl, substituted aryl, heterocyclo, substituted heterocyclo, heteroaryl, and substituted heteroaryl;
R$_6$, R$_7$ and R$_8$ are at each occurrence independently selected from hydrogen, alkyl, substituted alkyl, alkenyl, substituted alkenyl, halogen, cyano, nitro, —OR$_9$, —SR$_9$, —S(=O)R$_{11}$, —S(=O)$_2$R$_{11}$, —P(=O)$_2$R$_{10}$, —S(=O)$_2$OR$_{11}$, —P(=O)$_2$OR$_{10}$, —NR$_9$R$_{10}$, —NR$_9$S(=O)$_2$R$_{11}$, —NR$_9$P(=O)$_2$R$_{10}$, —S(=O)$_2$NR$_9$R$_{10}$, —P(=O)$_2$NR$_9$R$_{10}$, —C(=O)OR$_9$, —C(=O)R$_9$, —C(=O)NR$_9$R$_{10}$, —OC(=O)R$_9$, —OC(=O)NR$_9$R$_{10}$, —NR$_9$C(=O)OR$_{10}$, —NR$_{12}$C(=O)NR$_9$R$_{10}$, —NR$_{12}$S(=O)$_2$NR$_9$R$_{10}$, —NR$_{12}$P(=O)$_2$NR$_9$R$_{10}$, —NR$_9$C(=O)R$_{10}$, —NR$_9$P(=O)$_2$R$_{10}$, cycloalkyl, substituted cycloalkyl, aryl, substituted aryl, heterocyclo, substituted heterocyclo, heteroaryl, and substituted heteroaryl;
R$_9$, R$_{10}$, and R$_{12}$ are independently at each occurrence selected from hydrogen, alkyl, substituted alkyl, alkenyl, substituted alkenyl, cycloalkyl, substituted cycloalkyl, heterocycle, substituted heterocycle, aryl, substituted aryl, heteroaryl and substituted heteroaryl, or alternatively, R$_9$ and R$_{10}$ when attached to the same nitrogen atom as in —NR$_9$R$_{10}$ can be taken together to form a heterocyclo, heteroaryl, substituted heterocyclo, or substituted heteroaryl;
R$_{11}$ is selected from alkyl, substituted alkyl, alkenyl, substituted alkenyl, cycloalkyl, substituted cycloalkyl, heterocycle, substituted heterocycle, aryl, substituted aryl, heteroaryl and substituted heteroaryl;
or a pharmaceutically-acceptable salt thereof.

2. A compound according to claim 1, in which Q is selected from phenyl, napthyl, pyridyl, pyrazolyl, imidazolyl, triazolyl, furyl, thienyl, oxazolyl, isoxazolyl, thiazolyl, pyrrolyl, pyridazinyl, pyrimidinyl, pyrazinyl, and triazinyl, wherein each Q is optionally substituted with 0 to 1 R$_6$ and 0 to 2 R$_7$; or a pharmaceutically-acceptable salt thereof.

3. A compound according to claim 1, in which Q is phenyl or pyridyl optionally substituted with 0 to 1 R$_6$ and 0 to 2 R$_7$; or a pharmaceutically-acceptable salt thereof.

4. A compound according to claim 1, having the formula,

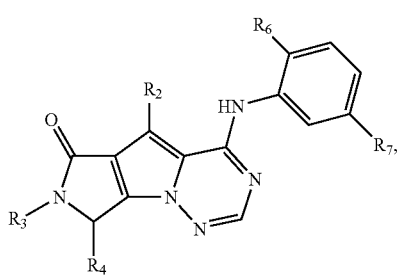

or a pharmaceutically-acceptable salt thereof.

5. A compound according to claim 4, wherein
R$_6$ is methyl or halogen;
R$_7$ is —C(O)NHR$_{10}$; and
R$_{10}$ is hydrogen, C$_{1-6}$alkyl, C$_{3-6}$cycloalkyl, isoxazolyl, and/or pyrazolyl wherein said isoxazolyl and/or pyrazolyl are optionally substituted with lower alkyl; or a pharmaceutically-acceptable salt thereof.

6. A compound according to claim 4, in which:
R$_2$ is C$_{1-4}$alkyl, C$_{1-4}$alkoxy, amino, cyano, halogen, or trifluoromethyl; and
R$_4$ is hydrogen; or a pharmaceutically-acceptable salt thereof.

7. A compound according to claim 1, in which Q is

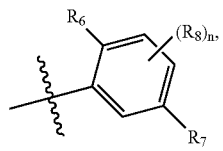

wherein n is 0 or 1; or a pharmaceutically-acceptable salt thereof.

8. A compound according to claim 7, in which
$R_6$ and $R_8$ are independently selected from lower alkyl, halogen, cyano, trifluoromethyl, lower alkoxy, and/or trifluoromethoxy;
$R_7$ is —C(O)NHR$_{10}$;
$R_{10}$ is hydrogen, $C_{1-6}$alkyl, $C_{3-6}$cycloalkyl, or optionally-substituted five membered heteroaryl; or a pharmaceutically-acceptable salt thereof.

9. A compound according to claim 1, in which $R_3$ is selected from lower alkyl optionally substituted with one to two of lower alkoxy, phenyl, pyridyl, or morpholinyl wherein said cyclic groups in turn are optionally substituted with one to two of lower alkyl, lower alkoxy, cyano, trifluoromethyl, trifluoromethoxy, and/or halogen; or a pharmaceutically-acceptable salt thereof.

10. A compound according to claim 1, in which:
$R_1$ is hydrogen;
$R_2$ is $C_{1-4}$alkyl;
$R_3$ is $C_{1-4}$alkyl or $C_{1-4}$alkyl substituted with one to two of halogen, amino, trifluoromethyl, trifluoromethoxy, hydroxy, $C_{1-6}$alkoxy, cyano, phenyl and/or pyridyl, said phenyl and/or pyridyl in turn being optionally substituted with one to two of lower alkyl, halogen, cyano, trifluoromethyl and/or lower alkoxy;
$R_4$ and $R_5$ are hydrogen;
$R_6$ is methyl or halogen;
$R_7$ is —C(O)NHR$_{10}$; and
$R_{10}$ is hydrogen, $C_{1-6}$alkyl, $C_{3-6}$cycloalkyl, and/or five-membered heteroaryl optionally substituted with lower alkyl; or a pharmaceutically-acceptable salt thereof.

11. A compound according to claim 1, in which:
$R_1$ is hydrogen; and
$R_4$ and $R_5$ are hydrogen; or a pharmaceutically-acceptable salt thereof.

12. A compound according to claim 1, having the formula,

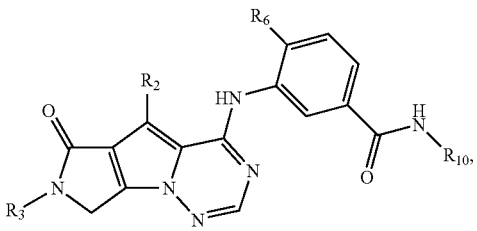

or a pharmaceutically-acceptable salt thereof.

13. A compound according to claim 12, in which:
$R_2$ is $C_{1-4}$alkyl;
$R_3$ is $C_{1-4}$alkyl or $C_{1-4}$alkyl substituted with one to two of halogen, amino, trifluoromethyl, trifluoromethoxy, hydroxy, $C_{1-6}$alkoxy, cyano, phenyl and/or pyridyl, in turn being optionally substituted with one to two of lower alkyl, halogen, cyano, trifluoromethyl, trifluoromethoxy, and/or lower alkoxy;
$R_6$ is methyl or halogen;
$R_{10}$ is hydrogen, $C_{1-6}$alkyl, $C_{3-6}$cycloalkyl, or heteroaryl optionally substituted with lower alkyl; or a pharmaceutically-acceptable salt thereof.

14. A compound according to claim 12, wherein $R_{10}$ is $C_{1-6}$alkyl or cyclopropyl.

15. A pharmaceutical composition comprising one or more compound according to claim 1 and a pharmaceutically-acceptable carrier or diluent.

16. A pharmaceutical composition comprising one or more compound according to claim 12 and a pharmaceutically-acceptable carrier or diluent.

17. A method of treating adult respiratory distress syndrome, chronic obstructive pulmonary disease, chronic pulmonary inflammatory disease, solid organ transplant rejection, atherosclerosis, and arthritis selected from rheumatoid arthrithis, psoriatic arthritis, traumatic arthritis, rubella arthritis, gouty arthristis and osteoarhtritis, comprising administering to a patient who is in need of an effective amount of a pharmaceutical composition according to claim 15.

* * * * *

UNITED STATES PATENT AND TRADEMARK OFFICE
CERTIFICATE OF CORRECTION

PATENT NO.        : 7,253,167 B2                                           Page 1 of 1
APPLICATION NO. : 11/170571
DATED             : August 7, 2007
INVENTOR(S)       : James Lin et al.

It is certified that error appears in the above-identified patent and that said Letters Patent is hereby corrected as shown below:

In the Claims - Column 48

Claim 13 - Line 19 - after "and/or pyridyl" insert --said phenyl and/or pyridyl--

Signed and Sealed this

Eleventh Day of March, 2008

JON W. DUDAS
*Director of the United States Patent and Trademark Office*